US008242273B2

(12) United States Patent  
Deng et al.

(10) Patent No.: US 8,242,273 B2
(45) Date of Patent: Aug. 14, 2012

(54) SYNTHESIS OF 4/5-PYRIMIDINYLIMIDAZOLES VIA SEQUENTIAL FUNCTIONALIZATION OF 2,4-DICHLOROPYRIMIDINE

(75) Inventors: Xiaohu Deng, San Diego, CA (US); Neelakandha Mani, San Diego, CA (US)

(73) Assignee: Janssen Pharmaceutica, NV, Beerse (BE)

( * ) Notice: Subject to any disclaimer, the term of this patent is extended or adjusted under 35 U.S.C. 154(b) by 104 days.

(21) Appl. No.: 12/831,037

(22) Filed: Jul. 6, 2010

(65) Prior Publication Data

US 2010/0274016 A1 Oct. 28, 2010

Related U.S. Application Data

(62) Division of application No. 11/494,060, filed on Jul. 27, 2006, now Pat. No. 7,807,832.

(60) Provisional application No. 60/703,078, filed on Jul. 28, 2005, provisional application No. 60/726,690, filed on Oct. 14, 2005.

(51) Int. Cl.
| C07D 401/00 | (2006.01) |
| C07D 403/00 | (2006.01) |
| C07D 405/00 | (2006.01) |
| C07D 409/00 | (2006.01) |
| C07D 411/00 | (2006.01) |
| C07D 413/00 | (2006.01) |
| C07D 417/00 | (2006.01) |
| C07D 419/00 | (2006.01) |

(52) U.S. Cl. ..................................... 544/331
(58) Field of Classification Search ................ None
See application file for complete search history.

(56) References Cited

U.S. PATENT DOCUMENTS

| 3,778,441 A | 12/1973 | Burckhardt et al. |
| 7,807,832 B2 * | 10/2010 | Deng et al. .................. 544/322 |
| 2005/0085473 A1 | 4/2005 | Van Hirschheydt et al. |

FOREIGN PATENT DOCUMENTS

| JP | 02072165 A2 | 3/1990 |
| WO | WO 01/37835 A1 | 5/2001 |
| WO | WO 01/38324 A2 | 5/2001 |
| WO | WO 02/088108 A1 | 11/2002 |
| WO | WO 02/088113 A1 | 11/2002 |
| WO | WO 03/087026 A1 | 10/2003 |

OTHER PUBLICATIONS

International Search Report dated Nov. 29, 2006 for corresponding Appln. No. PCT/US2006/029280.
Adams, J.L. et al. Pyrimidinylimidazole Inhibitors of p38: Cyclic N-1 Imidazole Substituents Enhance p38 Kinas Inhibition and Oral Activity. *Bioorg. Med. Chem. Lett.* 2001, 11, 2867-2870.
Banker et al., "Modern Pharmaceuticals", 1996, 596.
Bulman Page, P.C.; Rosenthal, S. A Simple and General Synthesis of α-Keto Esters. *Tetrahedron Lett.* 1986, 27, 1947-1950.
Chi, K.-W. et al. Palladium Catalyst in DMSO for the Oxidation of Tolans to Benzils. *Synth. Commun.* 1994, 24, 2119-2122.
Chu-Moyer, M.Y. et al. Orally-Effective, Long-Acting Sorbitol Dehydrogenase Inhibitors: Synthesis, Structure-Activity Relationships, and in Vivo Evaluations of Novel Heretocycle-Substituted Piperazino-Pyrimidines. *J. Med. Chem.* 2002, 45, 511-528.
Deng, X.; Mani, N. An Efficient Route to 4-Aryl-5-pyrmidinylimidazoles via Sequential Functionalization of 2,4-Dichloropyrimidine. *Org. Lett.* 2006, 8(2), 269-272.
De Dios A. et al., "Design of Potent and Selective 2-Aminobenzimidazole-based p38alpha MAP kinase Inhibitors with Excellent In Vivo Efficacy", *J Med Chem.*, 2005, 48(7), 2270-2273.
Dorwald F.A., "Side Reactions in Organic Synthesis", 2005, Wiley: VCH, Weinheim p. IX of Preface.
Frantz, D.E. et al. Synthesis of Substituted Imidazoles via Organocatalysis. *Org. Lett.* 2004, 6, 843-846.
Fullerton, T. et al. Suppression of ex Vivo Cytokine Production by SB-242235, A Selective Inhibitor of p38 MAP Kinase. *Clin. Pharmacol. Ther.* 2000, 67, 114, Abstract OI-B-4.
Holand, S.; Epsztein, R. Recherches sur les α-glycols acétyléniques. IV.—Etude du comportement des α-glycols α,α'-diacétyléniques diastéréoisomères en milieu alcalin. *Bull. Chim. Soc. Fr.* 1971, 5, 1694-1701.
Ito, S. et al. Synthesis and Self-Assembly of Functionalized Hexa-peri-hexabenzocoronenes. *Chem.—Eur. J.* 2000, 6, 4327-4342.
Kita, Y. et al. Hypervalent Iodine Oxidation of Ethynylcarbinols: A Short and Efficient Conversion of Dihydroxyacetonyl Groups from Keto Groups. *Chem. Pharm. Bull.* 1989, 37, 891-894.
Lee, D.G.; Chang, V.S. Oxidation of Hydrocarbons. 9. The Oxidation of Alkynes by Potassium Permanganate. *J. Org. Chem.* 1979, 44, 2726-2730.
Liverton, N.J. et al. Design and Synthesis of Potent, Selective, and Orally Bioavailable Tetrasubstituted Imidazole Inhibitors of p38 Mitogen-Activated Protein Kinase. *J. Med. Chem.* 1999, 42, 2180-2190.
Mangalagiu, I. Ethenylation and Alkynylation in Palladium-Catalyzed Carbosubstitution in Heteroazines. *Acta Chem. Scand.* 1996, 50, 914-917.
McIntyre, C.J. et al. Pyridazine Based Inhibitors of p38 MAPK. *Bioorg. Med. Chem. Lett.* 2002, 12, 689-692.
Minato, M. et al. Osmium Tetraoxide Catalyzed Vicinal Hydroxylation of Higher Olefins by Using Hexacyanoferrate(III) Ion as a Cooxidant. *J. Org. Chem.* 1990, 55, 766-768.
Mylari, B.L. et al. Sorbitol Dehydrogenase Inhibitors (SDIs): A New Potent, Enantiomeric SDI, 4-[2-1*R*-Hydroxy-ethyl)-pyrimidin-4-yl]-piperazine-1-sulfonic Acid Dimethylamide. *J. Med. Chem.* 2001, 44, 2695-2700.
Pattenden, G. et al. Facile Synthesis of the "Tricarbonyl" Subunit in the Immunosuppressant Rapamycin. *Tetrahedron Lett.* 1993, 34, 2677-2680.
Revesz, L. et al. Novel p38 Inhibitors with Potent Oral Efficacy in Several Models of Rheumatoid Arthritis. *Bioorg. Med. Chem. Lett.* 2004, 14(13), 3595-3599.

(Continued)

*Primary Examiner* — Jeffrey Murray

(57) ABSTRACT

This invention relates to methods of making pyrimidinyl-substituted imidazole compounds by sequential substitution of the 4- and 2-chloro groups of 2,4-dichloropyrimidine, nucleophilic substitution to form pyrimidinylalkyne derivatives, oxidation to the corresponding 1,2-diketones, and cyclocondensation reactions.

19 Claims, No Drawings

OTHER PUBLICATIONS

Sharpless, K.B. et al. Permanganate in Acetic Anhydride. α-Diketones Directly from Olefins. *J. Am. Chem. Soc.* 1971, 93, 3303-3304.

Sonogashira, K. et al. A Convenient Synthesis of Acetylenes: Catalytic Substitutions of Acetylenic Hydrogen with Bromoalkenes, Iodoarenes, and Bromopyridines. *Tetrahedron Lett.* 1975, 16(50), 4467-4470.

Srinivasan, N.S.; Lee, D.G. Preparation of 1,2-Diketones: Oxidation of Alkynes by Potassium Permanganate in Aqueous Acetone. *J. Org. Chem.* 1979, 44, 1574.

Tullis, J.S. et al. The Development of New Triazole Based Inhibitors of Tumor Necrosis Factor-α (TNF-α) Production. *Bioorg. Med. Chem. Lett.* 2003, 13, 1665-1668.

Van Leusen, A.M. et al. Base-Induced Cycloaddition of Sulfonylmethyl Isocyanides to C,N Double Bonds. Synthesis of 1,5-Disubstituted and 1,4,5-Trisubstituted Imidazoles from Aldimines and Imidoyl Chlorides. *J. Org. Chem.* 1977, 42, 1153-1159.

Walsh, C.J.; Mandel, B.K. Improved Synthesis of Unsymmetrical, Heteroaromatic 1,2-Diketones and the Synthesis of Carbazole Ring Substituted Tetraaryl Cyclopentadieneones. *J. Org. Chem.* 1999, 64, 6102-6105.

Wolff et al., "Burger's Medicinal Chemistry and Drug Discovery," 5th ed. Part I, 1995, pp. 975-977.

Yoshida, K; Taguchi, J. Reaction of N-Substituted Cyclic Amines with 2,4-Dichloroquinazoline, 2,4-Dichloropyrimidine, and its 5-Methyl Derivative. *J. Chem. Soc., Perkin Trans. 1* 1992, 7, 919-922.

Yusubov, M.S. et al. Chemoselective Oxidation of Carbon-Carbon Double or Triple Bonds to 1,2-Diketones with DMSO-Based Reagents. *Synthesis* 1995, 10, 1234-1236.

Yusubov, M.S. et al. Synthesis of Unsymmetrical Hetaryl-1,2-diketones. *Tetrahedron* 2002, 58, 1607-1610.

2-(2,6-Dichlorophenyl)-4,5-diarylimidazoles as c-Met Tyrosine Kinase Inhibitors. *iDrugs* 2003, 6(12), 1202.

\* cited by examiner

SYNTHESIS OF 4/5-PYRIMIDINYLIMIDAZOLES VIA SEQUENTIAL FUNCTIONALIZATION OF 2,4-DICHLOROPYRIMIDINE

This application is a divisional of U.S. patent application Ser. No. 11/494,060, filed on Jul. 27, 2006, now U.S. Pat. No. 7,807,832, which in turn claims the benefit of U.S. Provisional Patent Application Nos. 60/703,078, filed Jul. 28, 2005, and 60/726,690, filed Oct. 14, 2005, each of which is incorporated herein by reference in its entirety.

FIELD OF THE INVENTION

This invention relates to methods of making pyrimidinyl-substituted imidazole compounds. More particularly, this invention relates to methods of oxidizing pyrimidinyl alkynes to pyrimidinyl diketones, which are useful in the preparation of pyrimidinyl-substituted imidazole compounds.

BACKGROUND OF THE INVENTION 4,5-Diaryl-imidazoles, in which one of the aryl substituents is a heteroaryl group such as a pyridine or pyrimidine, form an important class of p38 MAPK (mitogen-activated protein kinase) inhibitors, reportedly pursued by a number of pharmaceutical companies as anti-inflammatory drugs (Fullerton, T. et al. *Clin. Pharmacol. Ther.* 2000, 67, 114). Examples of such pyrimidinyl imidazoles include:

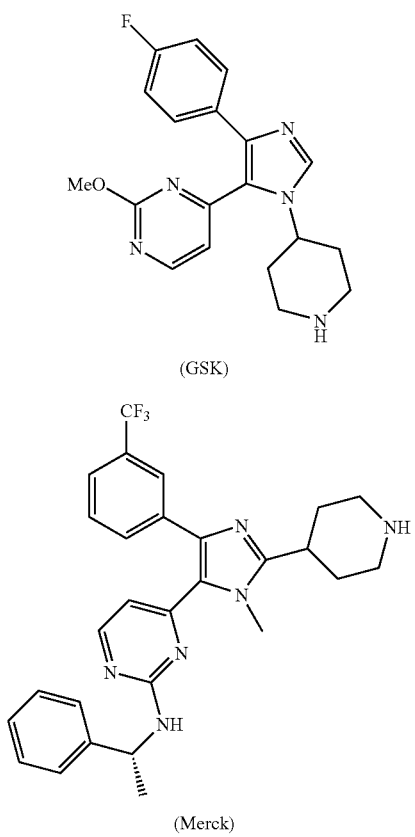

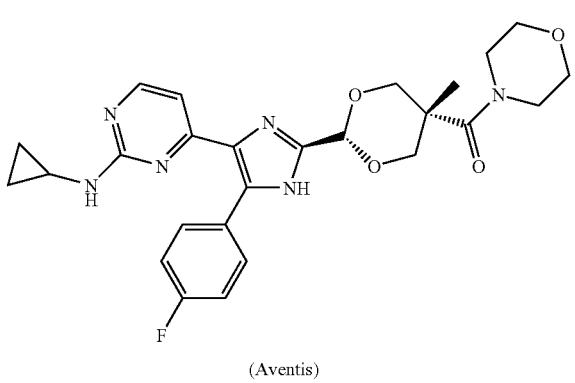

(Aventis)

Additional examples of such compounds include inhibitors of protein tyrosine kinases such as: c-Met tyrosine kinase and src kinase (See: U.S. Pat. Appl. Publ. 2005085473; Intl. Pat. Appl. Publ. WO03/087026) for the treatment of, for example, transplant rejection, inflammatory bowel syndrome, rheumatoid arthritis, psoriasis, restenosis, allergic asthma, Alzheimer's disease, Parkinson's disease, stroke, osteoporosis, cancer, and benign hyperplasia; and inhibitors of p38 MAP kinase as anti-cancer (Intl. Pat. Appl. Publ. WO03/087026) and anti-inflammatory agents (Revesz, L. et al. *Bioorg. Med. Chem. Lett.* 2004, 14(13), 3595-3599); inhibitors of B-raf kinase (Intl. Pat. Appl. Publ. WO01/038324) for the treatment of cancer and neuronal degeneration from ischemic events.

In spite of the heightened interest, preparation of these compounds has relied largely upon two synthetic strategies. Reported methodologies (Liverton, N. J. et al. *J. Med. Chem.* 1999, 42, 2180-2190; McIntyre, C. J. et al. *Bioorg. Med. Chem. Lett.* 2002, 12, 689-692) employed the cyclocondensation of substituted 1,2-dicarbonyl compounds with ammonia and an aldehyde. Although this reaction is quite efficient, preparation of the pyrimidinyl-substituted dicarbonyl derivatives reportedly proceeds through a lengthy sequence starting from 2-mercapto-4-methylpiperidine. Another approach (Adams, J. L. et al. *Bioorg. Med. Chem. Lett.* 2001, 11, 2867-2870, and literature cited therein) involved the cycloaddition of substituted TosMIC with aldimines, originally pioneered by van Leusen (Van Leusen, A. M. et al. *J. Org. Chem.* 1977, 42, 1153-1159). More recently, Merck scientists have reported a promising one-pot synthesis of imidazoles based on the cyclocondensation of an α-ketoamide with an amine, wherein the requisite α-ketoamide was generated in situ by a Stetter reaction involving an α-amidosulfone (Frantz, D. E. et al. *Org. Lett.* 2004, 6, 843-846). In these cases also, access to the suitably elaborated pyrimidines required multi-step sequences.

To successfully exploit the particularly efficient condensation of 1,2-diketones bearing an electron-deficient pyrimidine moiety with an aldehyde and ammonia, a more succinct route to the requisite 1,2-diketone derivatives would clearly be advantageous.

To more readily access the desired 1,2-diketone intermediates, we considered the oxidation of disubstituted acetylene compounds, which could be derived from the readily available 2,4-dichloropyrimidine through sequential substitution reactions (Scheme 1). Cyclocondensation of the resulting diketones of Formula (I) would provide the desired pyrimidinyl imidazoles. 1,2-Diketones of Formula (I) are useful in the preparation of pharmaceutically active pyrimidinyl imidazole compounds.

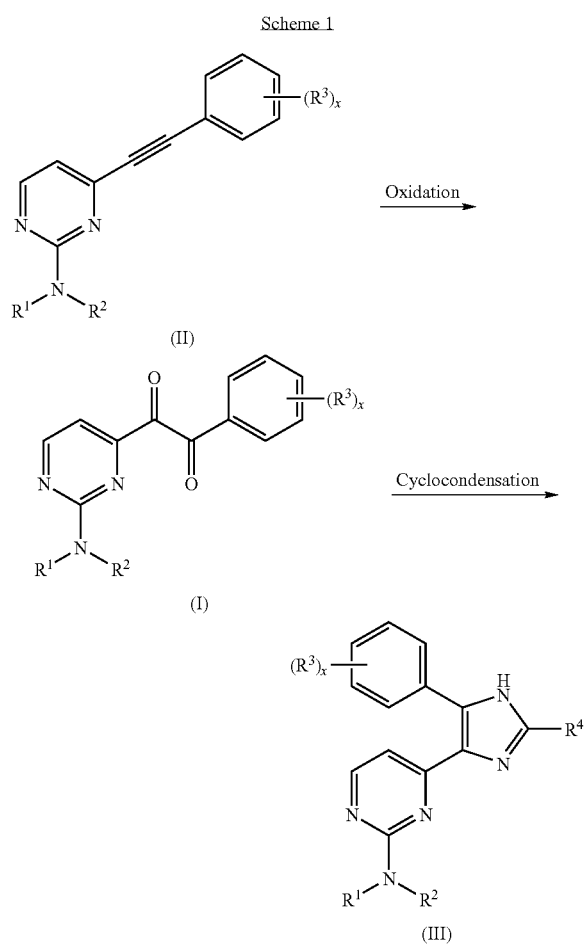

Scheme 1

SUMMARY OF THE INVENTION

Relative to existing methods, embodiments of the synthetic route according to this invention provide a concise methodology that is suitable for readily making a range of structurally related 1,2-diketone and imidazole analogs.

There are provided by the present invention methods of making amino substituted 1-(pyrimidin-4-yl)-2-phenyl-ethane-1,2-diones of Formula (I):

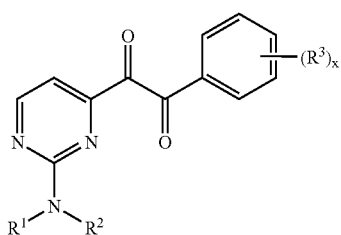

wherein:
$R^1$ and $R^2$ are each independently selected from the group consisting of —H, —$C_{1-6}$alkyl, —$C_{3-8}$cycloalkyl, benzyl, and 1-methylbenzyl;
x is 0, 1, 2, or 3; and
each $R^3$ is independently selected from the group consisting of —OH, —Cl, —F, —$C_{1-6}$alkyl, —$C_{3-8}$cycloalkyl, —$OC_{1-6}$alkyl, —$CF_3$, —$OCF_3$, phenyl, —CN, —$NO_2$, —N($R^a$)$R^b$, —C(O)N($R^a$)$R^b$, —N($R^c$)C(O)$R^d$, —N($R^c$)$SO_2C_{1-6}$alkyl, —C(O)$C_{1-6}$alkyl, —S(O)$_{0-2}C_{1-6}$alkyl, —$SO_2$N($R^a$)$R^b$, —$CO_2$H, and —$CO_2C_{1-6}$alkyl, where $R^a$ and $R^b$ are each independently —H or —$C_{1-6}$alkyl, and where $R^c$ and $R^d$ are each independently —H or —$C_{1-6}$alkyl;

and enantiomers, diastereomers, and pharmaceutically acceptable salts and esters thereof;

comprising oxidizing an alkyne of Formula (II):

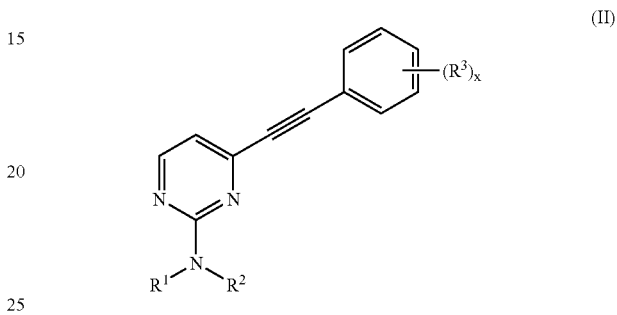

wherein $R^1$, $R^2$, $R^3$, and x are defined as above,
with finely powdered potassium permanganate.

The present invention further contemplates methods of making imidazoles of Formula (III):

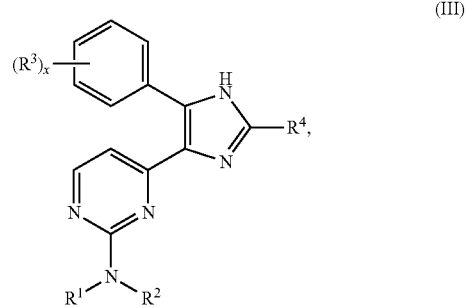

and tautomers thereof, wherein $R^1$, $R^2$, $R^3$, and x are defined as above; and $R^4$ is —H, —$C_{1-8}$alkyl, —$C_{3-8}$cycloalkyl, aryl, heteroaryl, heterocycloalkyl, or —CH(O$C_{1-6}$alkyl)$_2$;

comprising oxidizing an alkyne of Formula (II) to a 1,2-diketone of Formula (I) with finely powdered potassium permanganate. Reactions such as the oxidation of an alkyne of Formula (II) are performed in some embodiments of this invention in a buffered solution of suitable polarity that is chemically compatible with the reaction conditions.

The present invention further contemplates methods of making 4/5-pyrimidinylimidazoles comprising reacting 2,4-dichloropyrimidine with a nucleophilic-attack-protected-acetylene to form 2-chloro-4-(protected-ethynyl)pyrimidine.

The present invention further contemplates methods of making 4/5-pyrimidinylimidazoles comprising reacting 2,4-dichloropyrimidine with a compound of Formula (VII):

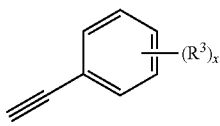

(VII)

to form a compound of Formula (VIII):

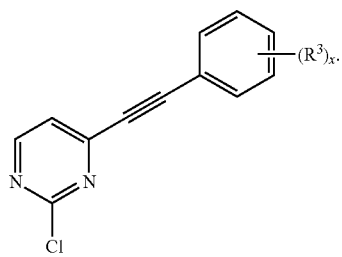

(VIII)

An object of the present invention is to overcome or ameliorate at least one of the disadvantages of the conventional methodologies and/or prior art, or to provide a useful alternative thereto.

DETAILED DESCRIPTION OF THE INVENTION

The invention may be more fully appreciated by reference to the following description, including the following glossary of terms and the concluding examples. For the sake of brevity, the disclosures of the publications cited in this specification are herein incorporated by reference.

As used herein, the terms "including", "containing" and "comprising" are used herein in their open, non-limiting sense.

The term "alkyl" refers to a straight- or branched-chain alkyl group having from 1 to 12 carbon atoms in the chain. Examples of alkyl groups include methyl (Me, which also may be structurally depicted by /), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples.

The term "alkylene" refers to a divalent straight- or branched-chain alkyl group having from 1 to 12 carbon atoms in the chain. Examples of alkylene groups include methylene, ethylene, propylene, and groups that in light of the ordinary skill in the art and the teachings provided herein would be considered equivalent to any one of the foregoing examples.

The term "alkenyl" refers to a straight- or branched-chain alkenyl group having from 2 to 12 carbon atoms in the chain. (The double bond of the alkenyl group is formed by two $sp^2$ hybridized carbon atoms.) Illustrative alkenyl groups include prop-2-enyl, but-2-enyl, but-3-enyl, 2-methylprop-2-enyl, hex-2-enyl, and groups that in light of the ordinary skill in the art and the teachings provided herein would be considered equivalent to any one of the foregoing examples.

The term "alkynyl" refers to a straight- or branched-chain alkynyl group having from 2 to 12 carbon atoms in the chain. (The triple bond of the alkynyl group is formed by two sp hybridized carbon atoms.) Illustrative alkynyl groups include prop-2-ynyl, but-2-ynyl, but-3-ynyl, 2-methylbut-2-ynyl, hex-2-ynyl, and groups that in light of the ordinary skill in the art and the teachings provided herein would be considered equivalent to any one of the foregoing examples.

The term "aryl" refers to a monocyclic or fused polycyclic, aromatic carbocycle (ring structure having ring atoms that are all carbon) having from 3 to 12 ring atoms per carbocycle. (Carbon atoms in aryl groups are $sp^2$ hybridized.) Illustrative examples of aryl groups include phenyl, naphthalenyl, anthracenyl, phenanthrenyl, and groups that in light of the ordinary skill in the art and the teachings provided herein would be considered equivalent to any one of the foregoing examples.

The term "heteroaryl" refers to a monocyclic, fused bicyclic, or fused polycyclic, aromatic heterocycle (ring structure having ring atoms selected from carbon atoms as well as nitrogen, oxygen, and sulfur heteroatoms) having from 3 to 12 ring atoms per heterocycle. Illustrative examples of heteroaryl groups include the following entities, in the form of properly bonded moieties:

and moieties that in light of the ordinary skill in the art and the teachings provided herein would be considered equivalent to any one of the foregoing examples.

The term "cycloalkyl" refers to a saturated or partially saturated, monocyclic or fused or spiro polycyclic, carbocycle having from 3 to 12 ring atoms per carbocycle. Illustrative examples of cycloalkyl groups include the following entities, in the form of properly bonded moieties:

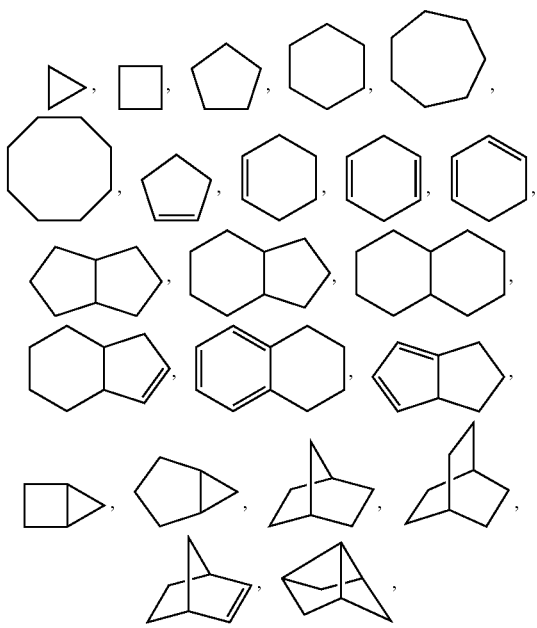

and moieties that in light of the ordinary skill in the art and the teachings provided herein would be considered equivalent to any one of the foregoing examples.

A "heterocycloalkyl" refers to a monocyclic, or fused or spiro polycyclic, ring structure that is saturated or partially saturated and has from 3 to 12 ring atoms per ring structure selected from C atoms and N, O, and S heteroatoms. Illustrative examples of heterocycloalkyl groups include the following entities, in the form of properly bonded moieties:

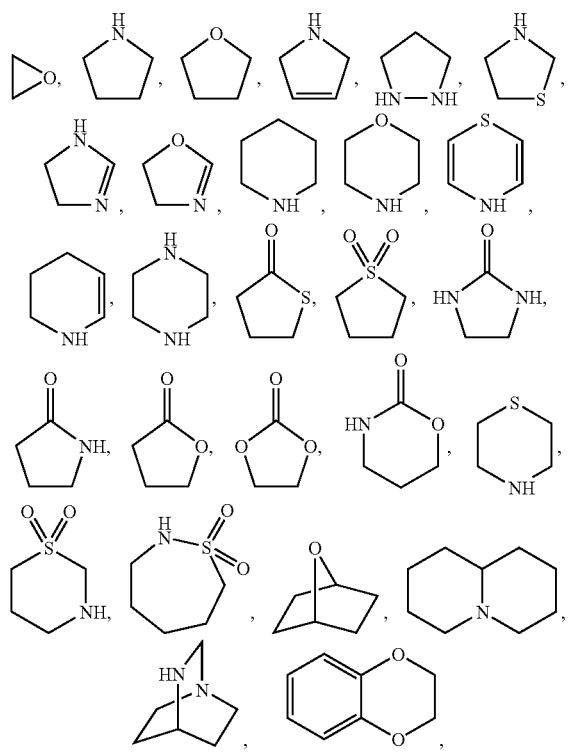

and moieties that in light of the ordinary skill in the art and the teachings provided herein would be considered equivalent to any one of the foregoing examples.

The term "halogen" represents chlorine, fluorine, bromine or iodine. The term "halo" represents chloro, fluoro, bromo or iodo.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valence allowed position on the system. It is understood that substitutions and combinations of substitutions recited herein, whether stated explicitly or not, refer to substitutions that are consistent with the valence of the member being substituted. Terms such as "valence allowed", "valence allowed site", "valence allowed member" and morphological variations thereof are used herein in this sense. For example, "valence allowed" when applied to a carbon member refers to the tetravalency of C; it refers to the trivalency of N when applied to a nitrogen member; and it refers to the bonding of a nitrogen member that is conventionally characterized with a positive electric charge or that is in a quaternary form. The present invention also encompasses compounds as described herein and equivalents thereof with at least one valence allowed nitrogen member, including but not limited to a quaternary nitrogen member and a nitrogen oxide. Such quaternary nitrogen member can be generated with a known agent for this purpose, such as lower alkyl halides, dialkyl sulfates, long chain halides, and aralkyl halides. Valence allowed options are part of the ordinary skill in the art.

Any formula given herein is intended to represent compounds having structures depicted by the structural formula as well as certain variations or forms. In particular, compounds of any given formula given herein may have asymmetric centers and therefore exist in different enantiomeric forms. All optical isomers and stereoisomers of the compounds of the general formula, and mixtures thereof, are considered within the scope of the formula. Thus any given formula given herein is intended to represent a racemate, one or more enantiomeric forms, one or more diastereomeric forms, one or more atropisomeric forms, and mixtures thereof.

Furthermore, certain structures may exist as geometric isomers (i.e., cis and trans isomers), as tautomers, or as atropisomers. Additionally, any formula given herein is intended to represent hydrates, solvates, and polymorphs, and mixtures thereof when such forms exist in the medium.

The term "4/5-pyrimidinylimidazole" as used herein refers to an imidazole ring where the pyrimidinyl substituent is in the 4- or the 5-position in the imidazole ring, and it also refers to the pair of pyrimidinyl imidazole tautomers. It is known that substituted imidazoles can interconvert due to tautomerism, and that one tautomeric form (for example the 4-substituted) may appear as the predominant form in a certain medium whereas the other tautomeric form (for example the 5-substituted) may appear as the predominant form in a different medium. It is understood that, unless specified otherwise, reference to a substituted imidazole, whether referred to as 4/5 substituted imidazole or not, refers to and encompasses whichever tautomeric form is present in the medium, and if both tautomers are present in such medium, then it refers to and encompasses both tautomers. This lexicography also applies to the chemical structures given herein. Accordingly, a chemical structure that displays the imidazole moiety given as

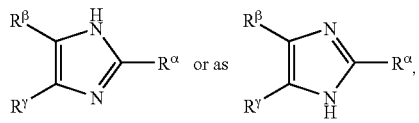

refers to any one of the tautomers or to the tautomer pair, depending on whether one tautomer, the other tautomer or the pair is present in the medium. ($R^\alpha$, $R^\beta$, and $R^\gamma$ in these tautomeric structures are generic substituents that refer to any one of the imidazole substituents/moieties referred to herein).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, sulfur, fluorine, chlorine, and iodine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{125}I$, respectively. Such isotopically labelled compounds are useful in metabolic studies (preferably with $^{14}C$), reaction kinetics studies (with, for example $^2H$ or $^3H$), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly preferred for PET or SPECT studies. Further, substitution with heavier isotopes such as deuterium (i.e., $^2H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the moiety for the variable appearing elsewhere. In other words, where a variable appears more than once, the choice of the species from a specified list is independent of the choice of the species for the same variable elsewhere in the formula, unless stated otherwise.

By way of a first example on substituent terminology, if substituent $S^1_{example}$ is one of $S_1$ and $S_2$, and substituent $S^2_{example}$ is one of $S_3$ and $S_4$, then these assignments refer to embodiments of this invention given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S_2$, and $S^2_{example}$ is one of $S_3$ and $S_4$" is accordingly used herein for the sake of brevity, but not by way of limitation. The foregoing first example on substituent terminology, which is stated in generic terms, is meant to illustrate the various substituent assignments described herein. The foregoing convention given herein for substituents extends, when applicable, to members such as $R^{1-4}$, $R^{1'-4'}$ and x, and any other generic substituent symbol used herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$, and $S_3$" is accordingly used herein for the sake of brevity, but not by way of limitation. The foregoing second example on substituent terminology, which is stated in generic terms, is meant to illustrate the various substituent assignments described herein. The foregoing convention given herein for substituents extends, when applicable, to members such as $R^{1-4}$, $R^{1'-4'}$ and x, and any other generic substituent symbol used herein.

The nomenclature "$C_{i-j}$" with j>i, when applied herein to a class of substituents, is meant to refer to embodiments of this invention for which each and every one of the number of carbon members, from i to j including i and j, is independently realized. By way of example, the term $C_{1-3}$ refers independently to embodiments that have one carbon member ($C_1$), embodiments that have two carbon members ($C_2$), and embodiments that have three carbon members ($C_3$).

The term $C_{n-m}$ alkyl refers to an aliphatic chain, whether straight or branched, with a total number N of carbon members in the chain that satisfies $n \leq N \leq m$, with m>n.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

"Finely powdered" potassium permanganate refers to this compound in a form that is recognized in the manufacturing and marketing of this compound with this characterization. An example of finely powdered potassium permanganate is the product Cairox M®, marketed by Carus Chemical Company. Embodiments of finely powdered potassium permanganate include forms of this compound that have a particle size of at least 325 mesh. In one illustrative embodiment, finely powdered potassium permanganate is provided in samples that completely pass through #325 standard sieve (44 micron). Preferably, potassium permanganate is of at least 98% purity.

The terms "buffered" solution or "buffer" solution are used herein interchangeably according to their standard meaning. Buffered solutions are used to control the pH of a medium, and their choice, use, and function is known to those of ordinary skill in the art. See, for example, G. D. Considine, ed., Van Nostrand's Encyclopedia of Chemistry, p. 261, 5$^{th}$ ed. (2005), describing, inter alia, buffer solutions and how the concentrations of the buffer constituents relate to the pH of the buffer. See also Handbook of Chemistry and Physics, 84$^{th}$ ed., pp. 8-37 to 8-44. For example, a buffered solution is obtained by adding $MgSO_4$ and $NaHCO_3$ to a solution in a 10:1 w/w ratio to maintain the pH of the solution at about 7.5.

Solutions used in embodiments of this invention are exemplified by those that have one or more miscible solvents that are chemically compatible with the reaction conditions, preferably unreactive with permanganate, and that provide a medium that has a dielectric constant comparable with that of the examples given herein. For example, acetone/$H_2O$ solutions provide examples of embodiments of solution media in embodiments of this invention. Acetone is a convenient and readily available solvent that does not interfere with the reaction conditions, and is miscible with water in the proportions desired to achieve a suitable medium polarity for embodiments of this invention. Dielectric constants for solvents and other liquids are readily available from standard reference materials, such as the Handbook of Chemistry and Physics. One of ordinary skill in the art should be able to replace acetone/water mixtures with other mixtures based on the teachings provided herein and available reference materials.

Embodiments of acetone/water solutions include any mixture thereof. Preferably, an acetone/$H_2O$ solution is obtained by mixing acetone and water in a volume ratio of from about 3:1 to about 5:6, more preferably from about 8:3 to about 6:5, and more preferably about 1.75:1. Other solvents can be used instead of acetone in other embodiments of this invention, and other solvents can be used together with acetone and water in still other embodiments of this invention, provided that such media have the suitable polarity and chemical compatibility properties under the reaction conditions, as such properties are exemplified herein and equivalents thereof.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Reference to a compound herein stands for a reference to any one of: (a) the actually recited form of such compound, and (b) any of the forms of such compound in the medium in which the compound is being considered when named. For example, reference herein to a compound such as R—COOH, encompasses reference to any one of, for example, R—COOH$_{(s)}$, R—COOH$_{(sol)}$, and R—COO$^-$$_{(sol)}$. In this example, R—COOH$_{(s)}$ refers to the solid compound, as it could be for example in a tablet or some other solid pharmaceutical composition or preparation; R—COOH$_{(sol)}$ refers to the undissociated form of the compound in a solvent, such as water; and R—COO$^-$$_{(sol)}$ refers to the dissociated form of the compound in a solvent, such as the dissociated form of the compound in an aqueous environment, whether such dissociated form derives from R—COOH, from a salt thereof, or from any other entity that yields R—COO$^-$ upon dissociation in the medium being considered. In another example, expressions such as "exposing an entity to compound of formula R—COOH", "reacting an entity with R—COOH", and analogous expressions refer to the exposure of such entity to the form, or forms, of the compound R—COOH that exists, or exist, in the medium in which such exposure and/or reaction takes place. In this regard, if such entity is for example in an aqueous environment, it is understood that the compound R—COOH is in such same medium, and therefore the entity is being exposed to species such as R—COOH$_{(aq)}$ and/or R—COO$^-$$_{(aq)}$, where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, ammonia and ammonium compounds, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. No further examples in this regard are provided herein because these interactions and transformations in a given medium are known by any one of ordinary skill in the art.

To obtain the various compounds described herein and equivalents thereof, starting materials may be employed that carry the ultimately desired substituents through the reaction scheme with or without protection as appropriate. Alternatively, it may be necessary to employ, in the place of the ultimately desired substituent, a suitable group that may be carried through the reaction scheme and replaced as appropriate with the desired substituent.

During any of the processes for preparation of the compounds of the present invention, it may be necessary and/or desirable to protect sensitive or reactive groups on any of the molecules concerned. In addition, compounds of the invention may be modified by using protecting groups; such compounds, precursors, or prodrugs are also within the scope of the invention. This may be achieved by means of conventional protecting groups, such as those described in "Protective Groups in Organic Chemistry", ed. J. F. W. McOmie, Plenum Press, 1973; and T. W. Greene & P. G. M. Wuts, "Protective Groups in Organic Synthesis", 3$^{rd}$ ed., John Wiley & Sons, 1999; further examples of protecting groups are well known in organic synthesis and the peptide art, and are described by M. Bodanzsky, *Principles of Peptide Synthesis,* 1st and 2nd revised ed., Springer-Verlag, New York, 1984 and 1993; Stewart and Young, Solid *Phase Peptide Synthesis,* 2nd ed., Pierce Chemical Co, Rockford, Ill. 1984; L. Fieser and M. Fieser, *Fieser and Fieser's Reagents for Organic Synthesis,* John Wiley and Sons (1994); L. Paquette, ed., *Encyclopedia of Reagents for Organic Synthesis,* John Wiley and Sons (1995). Amino protecting groups are also given in, e.g., WO 98/07685. The protecting groups may be removed at a convenient subsequent stage by using methods known from the art. One or more than one protecting groups may often be used in a protection/deprotection operation. The choice typically intends to provide a protected group that will be stable under the conditions of subsequent reactions, and that can be removed at an appropriate step without disrupting the rest of the compound.

The methods of making imidazoles of Formula (III) may further comprise reacting, in the presence of an ammonia equivalent, a 1,2-diketone of Formula (I) with $R^4$CHO, where $R^4$ is defined as above, or with a formaldehyde equivalent.

Suitable formaldehyde equivalents include hexamethylenetetramine, formaldehyde, and the like, and mixtures thereof. Suitable ammonia equivalents include ammonia, ammonium salts such as ammonium acetate and the like, and mixtures thereof.

The present invention further contemplates methods of making compounds of Formula (I), comprising at least one of:

a) reacting 2,4-dichloropyrimidine with (trimethylsilyl) acetylene to form 2-chloro-4-trimethylsilanylethynyl-pyrimidine;

b) reacting 2-chloro-4-trimethylsilanylethynyl-pyrimidine with $R^1R^2NH$ to form a (trimethylsilyl)alkyne of Formula (IV):

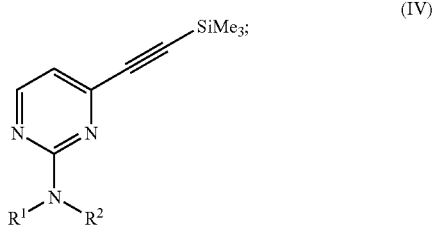
(IV)

c) deprotecting a (trimethylsilyl)alkyne of Formula (IV) to form an alkyne of Formula (V):

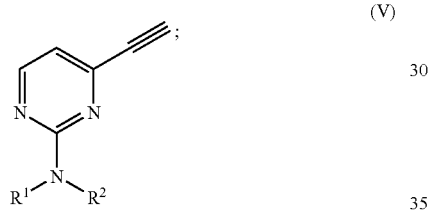
(V)

and d) reacting an alkyne of Formula (V) with a compound of Formula (VI):

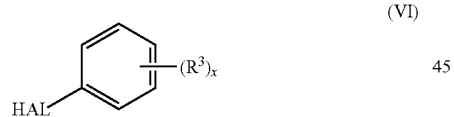
(VI)

to form a compound of Formula (II);
wherein $R^1$, $R^2$, $R^3$, and x are defined as above; and HAL is I or Br.

The present invention further contemplates methods of making compounds of Formula (I), comprising at least one of:

a) reacting 2,4-dichloropyrimidine with a compound of Formula (VII):

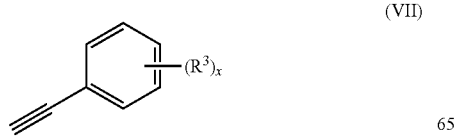
(VII)

to form a compound of Formula (VIII):

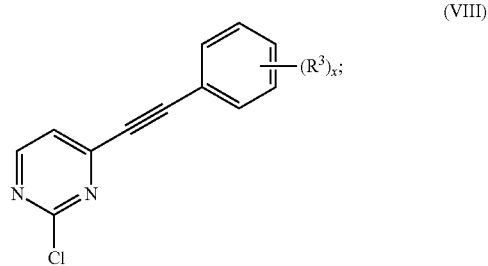
(VIII)

and b) reacting a compound of Formula (VIII) with $R^1R^2NH$ to form a compound of Formula (II), wherein $R^1$, $R^2$, $R^3$, and x are defined as above.

In more particular embodiments, the retrosynthetic scheme may be represented by Scheme 2.

Scheme 2

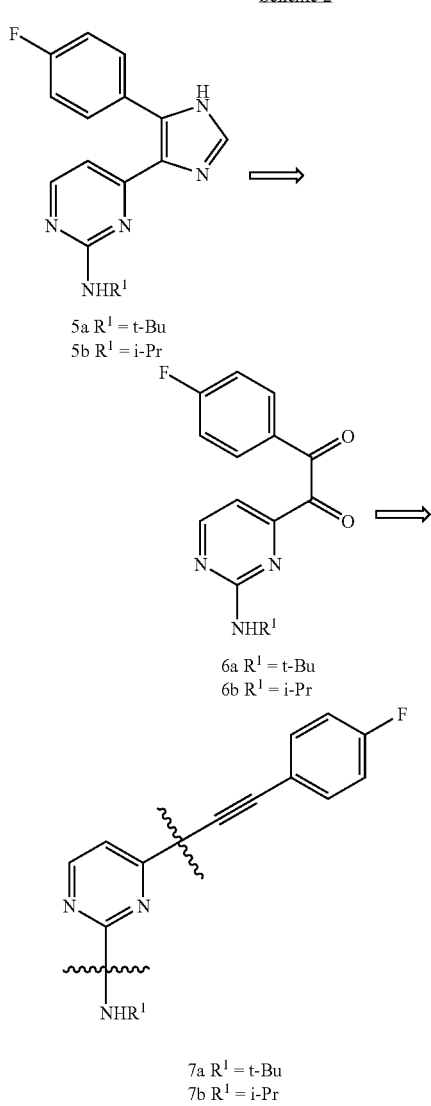

5a $R^1$ = t-Bu
5b $R^1$ = i-Pr

6a $R^1$ = t-Bu
6b $R^1$ = i-Pr

7a $R^1$ = t-Bu
7b $R^1$ = i-Pr

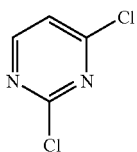

The preparation of the 1,2-diarylalkynes is described in Schemes 3-5.

Initial attempts to perform selective substitution, outlined in Scheme 3, did not produce encouraging results. Reacting 2,4-dichloropyrimidine with t-butyl amine at 60° C. gave a mixture of 4- and 2-substitution products in 65% and 26% yield respectively. This result clearly indicated that the chloro group at the 4-position is more reactive (albeit slightly) toward substitution with amine nucleophiles than the 2-position (Mylari, B. L. et al. *J. Med. Chem.* 2001, 44, 2695-2700; Yoshida, K.; Taguchi, M. *J. Chem. Soc., Perkin Trans.* 1 1992, 7, 919-22; Chu-Moyer, M. Y. et al. *J. Med. Chem.* 2002, 45, 511-528). Although a variety of base and solvent combinations were investigated, no synthetically useful 2-position selectivity was found. On smaller scale (5-10 g), the two regioisomers can be separated by column chromatography. The 4-chloro regioisomer can then be reacted with 4-fluorophenylacetylene, under standard Sonogashira coupling conditions (Sonogashira, K. et al. *Tetrahedron Lett.* 1975, 50, 4467-4470), to furnish the desired disubstituted acetylene 7a in 76% yield. Although we obtained diarylacetylene 7a in two steps, the poor regioselectivity in the nucleophilic substitution reaction rendered this approach impractical for large-scale synthesis.

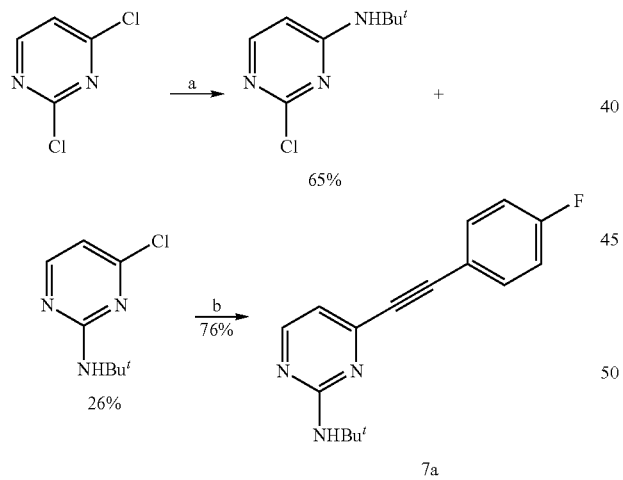

Scheme 3

Conditions: (a) NH$_2$Bu$^t$, neat, reflux; (b) 1-ethynyl-4-fluorobenzene, Pd(PPh$_3$)$_2$Cl$_2$/CuI, THF/Et$_3$N, reflux.

By reversing the order of the substitution steps, we overcame the regioselectivity issues. We found that a Sonogashira reaction between 2,4-dichloropyrimidine and 1-ethynyl-4-fluorobenzene smoothly afforded the desired regioisomer 8 as the major product (Scheme 4). Unfortunately, nucleophilic substitution of the 2-chloro substituent with tert-butylamine gave a mixture of the desired compound 7a, along with alkyne adduct 9. The structure of 9 was ascertained by nuclear Overhauser effect (NOE) experiments. To avoid this hydroamination reaction, a variety of conditions, such as Na$_2$CO$_3$/EtOH, Et$_3$N/THF, NH$_2$Bu$^t$/THF, and Buchwald amination, were investigated without much success. However, where amines other than tert-butylamine are used in this transformation, e.g. isopropylamine, yields and regioselectivity are much improved. Reactions using embodiments of amines R$^1$R$^2$NH that are not tert-butylamine may be preferably accomplished using R$^1$R$^2$NH as the solvent, or in a solvent such as THF or DMF, at temperatures between room temperature and 80° C.

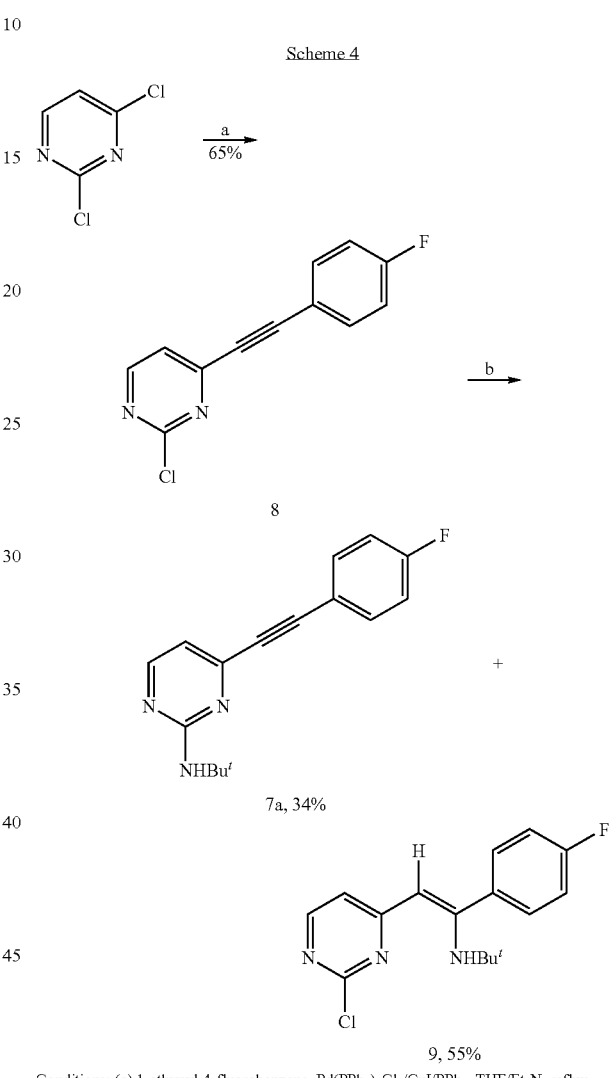

Scheme 4

Conditions: (a) 1-ethynyl-4-fluorobenzene, Pd(PPh$_3$)$_2$Cl$_2$/CuI/PPh$_3$, THF/Et$_3$N, reflux, 3 h; (b) NH$_2$Bu$^t$, sealed tube, 80° C.

As shown in Scheme 5, a new route was designed: Sonogashira cross-coupling reaction of a nucleophilic-attack-protected acetylene, such as [(tri-4-alkyl)silyl]acetylene, for example (trimethylsilyl)acetylene, with 2,4-dichloropyrimidine gave good regioselectivity in excellent yield. Yields of about 87% were achieved in embodiments of this invention. Heating in neat t-butylamine at 80° C. gave the desired substitution product. It is understood that the SiMe$_3$ protection group in Scheme 5 is replaced in other embodiments of this invention by any other protection group that provides similar protective effects to a nucleophilic attack to the alkyne moiety. Such protective groups are referred to herein as "nucleophilic-attack protectors". A nucleophilic-attack-protected acetylene is an acetylene with one of such protective groups attached to one of its ends, and a 2-chloro-4-protected-ethynyl-pyrimidine is a compound analogous to 10 with a nucleophilic-attack protector attached to the acetylenic moiety instead of the SiMe$_3$ given in compound 10. Nucleophilic-attack protectors for alkyne groups are well known. See for example, Greene and Wuts, Protective Groups in Organic Synthesis, 3$^{rd}$ ed., chapter 8, which is incorporated herein by reference. Examples of such protection groups are trialkylsilanes, including, but not limited to, (tri-C$_{1-4}$alkyl)silanes such as SiPG$^1$PG$^2$PG$^3$, wherein each one of PG$^1$, PG$^2$, and PG$^3$ is chosen independently from the other PG groups from the group of C$_{1-4}$alkyl, wherein "alkyl" refers to a straight- or branched-chain alkyl that has a number of carbon members ranging from one to four. Specific examples of alkyne protecting groups are provided by TMS (trimethylsilyl), TES (triethylsilyl), TBDMS (t-butyldimethylsilyl), TDS (thexyldimethylsilyl), DOPS (dimethyl[1,1-dimethyl-3-(tetrahydro-2H-pyran-2-yloxy)propylsilyl), BDMS (biphenyldimethylsilyl), TIPS (triisopropylsilyl), biphenyldiisopropylsilyl), and Me$_2$C(OH) (2-(2-hydroxypropyl)). Finally, desilylation followed by another Sonogashira cross-coupling with 4-fluoro-iodobenzene afforded compound 7a in very good overall yield. This reaction sequence was performed successfully on 20-40 g scale without the need for column chromatography. Accessing intermediate 10 as taught herein affords a more efficient route to 7a and also allows for a point of diversification for the design of new analogues. This is a desirable feature for certain applications, such as medicinal chemistry applications and the making of libraries of compounds. In contrast, conventional methodologies direct the synthetic focus to the formation of a 1,2-diketone. It is to be noted that accessing intermediate 10 as taught herein provides a step that can be implemented in the synthesis of any 4/5-pyrimidinylimidazole, as long as basic principles of chemical compatibility are satisfied. This applicability range is due to the fact that the formation of intermediate 10 as taught herein is independent of and takes place prior to the formation of the eventual imidazole ring.

triple bond less electron deficient and more sterically encumbered are contributing factors to the results obtained in embodiments of this invention, so that the nucleophilic substitution preferentially on the pyrimidine nucleus is effected.

With a reliable route to di-arylsubstituted acetylenes 7a and 8 in hand, we set out to examine the oxidation reaction. Initially, we focused our attention on the oxidation of entity 8, for it would allow the introduction of the amine substituent after imidazole formation. Oxidation of diarylsubstituted acetylene to diketone is well precedented and wide array of reagent systems have been reported (Holland, S.; Epsztein, R. Bull. Chim. Soc. Fr. 1971, 1694; Walsh, C. J.; Mandal, B. K. J. Org. Chem. 1999, 64, 6102-6105; Yusubov, M. S. et al. Tetrahedron 2002, 58, 1607-1610). However, oxidation of a diarylacetylene containing a pyrimidine group proved complex and difficult to achieve, as illustrated by the attempts to oxidize entity 8 by using a battery of reagent systems, attempts that resulted in no oxidation or over-oxidation (Table 1) despite the experience reported in reference teachings (Chi, K-W. et al. Synth. Commun. 1994, 24, 2119). In contrast, in the case of entity 7a, oxidation using KMnO$_4$ or PdCl$_2$ went smoothly on small scale (Table 1, entries 3 and 5). The stark reactivity difference between entities 7a and 8 could be due to the reduced electron-deficiency of the triple bond in compound 7a.

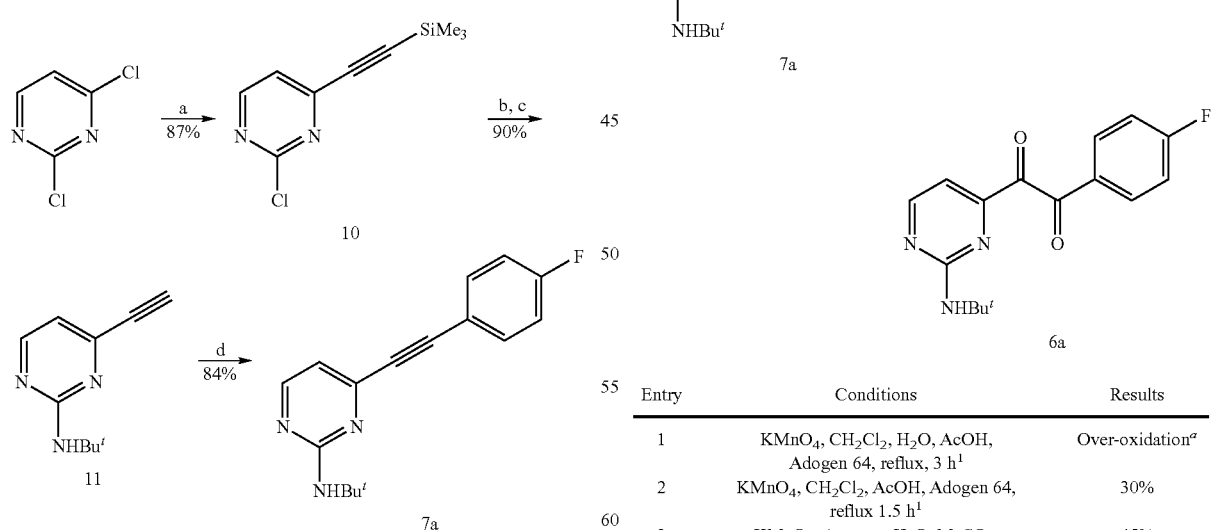

TABLE 1

Oxidation of compound 7a.

| Entry | Conditions | Results |
|---|---|---|
| 1 | KMnO$_4$, CH$_2$Cl$_2$, H$_2$O, AcOH, Adogen 64, reflux, 3 h[1] | Over-oxidation[a] |
| 2 | KMnO$_4$, CH$_2$Cl$_2$, AcOH, Adogen 64, reflux 1.5 h[1] | 30% |
| 3 | KMnO$_4$, Acetone, H$_2$O, MgSO$_4$, NaHCO$_3$, rt, 45 min[2] | 45% |
| 4 | I$_2$/DMSO, 150° C., 16 h[3] | Over-oxidation[a] |
| 5 | PdCl$_2$/DMSO, 130° C., 4 h[4] | 53% |
| 6 | NBS/DMSO, rt, 10 min[4] | Bromination[b] |
| 7 | HBr/DMSO, 130° C., 3 h[5] | Bromination[b] |
| 8 | (CF$_3$COO)$_2$IPh, DMSO, 130° C., 3 h[6] | No reaction |

The synthetic methodology developed in the context of this invention is not limited by specific theories for the underlying reaction steps. It is believed, however, that the making of the

TABLE 1-continued

Oxidation of compound 7a.

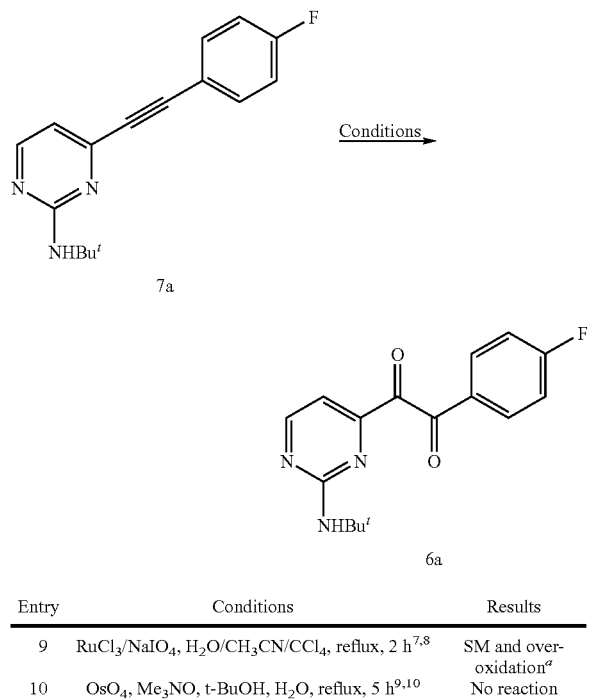

| Entry | Conditions | Results |
|---|---|---|
| 9 | RuCl$_3$/NaIO$_4$, H$_2$O/CH$_3$CN/CCl$_4$, reflux, 2 h[7,8] | SM and over-oxidation[a] |
| 10 | OsO$_4$, Me$_3$NO, t-BuOH, H$_2$O, reflux, 5 h[9,10] | No reaction |

[a]4-Fluorobenzoic acid was isolated.
[b]Based on MS, the product was not isolated.
References for Table 1:
[1]Lee, D.G.; Chang, V.S. J. Org. Chem. 1979, 44, 2726-2730.
[2]Srinivasan, N.S.; Lee, D.G. J. Org. Chem. 1979, 44, 1574.
[3]Dötz, F.; Brand, J.D.; Ito, S.; Gherghel, L.; Müllen, K. J. Am. Chem. Soc. 2000, 122, 7707-7717; Ito, S.; Wehmeier, M.; Brand, J.D.; Kubel, C.; Epsch, R.; Rabe, J.P.; Mullen, K. Chem. -Eur. J. 2000, 6, 4327-4342.
[4]Chi, K-W; Yusubov, M.S.; Filimonov, V.D. Synth. Commun. 1994, 24, 2119.
[5]Yusubov, M.S.; Filimonov, V.D.; Vasilyeva, V.P.; Chi, K-W. Synthesis 1995, 10, 1234-1236.
[6]Kita, Y.; Yakura, T.; Terashi, H.; Haruta, J.; Tamura, Y. Chem. Pharm. Bull. 1989, 37, 891-894.
[7]Sharpless, K.B.; Lauer, R.F.; Repic, O.; Teranishi, A.Y.; Williams, D.R. J. Am. Chem. Soc. 1971, 93, 3303;
[8]Pattenden, G.; Tankard, M.; Cherry, P.C. Tetrahedron Lett. 1993, 34, 2677-2680.
[9]Minato, M.; Yamamoto, K.; Tsuji, J. J. Org. Chem. 1990, 55, 766-768.
[10]Page, P.C.B.; Rosenthal, S. Tetrahedron Lett. 1986, 27, 1947-1950.

The oxidation procedures using KMnO$_4$ and PdCl$_2$ were further investigated. In contrast with the KMnO$_4$ oxidation, the PdCl$_2$/DMSO oxidizing system exhibited drawbacks, requiring high Pd loading (~10%), prolonged reaction time, and elevated temperatures (130° C.) to achieve reasonably good conversion. Lower Pd loading caused incomplete reaction and raising the temperature caused side reactions. A Pd on C/CuCl$_2$/DMSO system produced similar results (Yusubov, M. S. et al. *Synthesis* 1995, 10, 1234-1236). These methods also required column chromatography to purify the final product, making them less well-suited for large-scale preparations. Although oxidation using KMnO$_4$ was more promising in terms of clean reaction and easy purification, over oxidation was a major disadvantage. Preparation of 1,2-diketones by oxidizing alkynes with finely powdered potassium permanganate has been reported (Srinivasan, N. S. et al. *J. Org. Chem.* 1979, 44(9), 1574) for a small class of 1,2-diketones that are unrelated to the compounds synthesized according to the present invention. These reference teachings on the use of potassium permanganate do not teach or suggest the selection of the entities to be oxidized according to this invention, and they do not teach or suggest the specific oxidation reactions that will accomplish such oxidation with the features of the methodology according to this invention. After screening numerous conditions, it was found that the key to obtaining good yields with the chemical entities of this invention was to use finely powdered KMnO$_4$ and to control the reaction time while the reaction was proceeding in a buffered solution. In some embodiments the finely powdered KMnO$_4$ was KMnO$_4$ (Cairox M®), purchased from Carus Chemical Company. An example of such buffered solution used in embodiments of this invention is an acetone/H$_2$O solution buffered with MgSO$_4$ and NaHCO$_3$. The buffering is preferably performed in embodiments of this invention to control the pH in the range from about 7 to about 8. Some embodiments of this invention were performed with the oxidation being performed in a solution buffered at a pH of about 7.5. Under these optimized conditions, the desired diketone 6a was obtained consistently in 65-70% yields on 5-g scale after simple aqueous workup and without column chromatography.

Many literature methods have been reported that efficiently oxidize simple diphenylacetylene compounds. A variety of these methods were examined to oxidize pyrimidinyl-substituted acetylene analogs, but were not successful. Therefore, based on the application of conventional methods from the literature and the poor results as applied to compounds of Formula (I), the success of the finely powdered KMnO$_4$ procedure was unexpected.

Reaction control was achieved by monitoring the reaction and quenching it by the addition of NaHSO$_3$ when complete.

Using the method described above, iso-propyl analog 6b was also prepared in good yield. Cyclocondensation of the diketones with ammonium acetate and an aldehyde efficiently provided various pyrimidinyl-substituted imidazoles.

Scheme 6

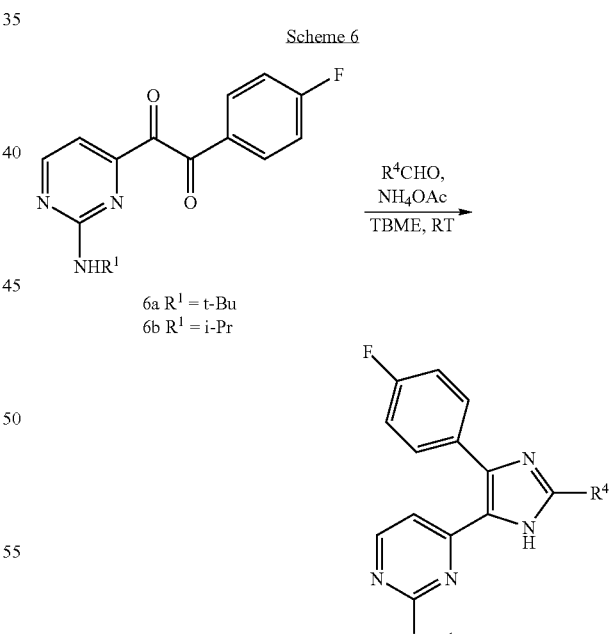

6a R$^1$ = t-Bu
6b R$^1$ = i-Pr

7a R$^1$ = t-Bu, R$^4$ = H
7b R$^1$ = i-Pr, R$^4$ = H
7c R$^1$ = i-Pr, R$^4$ = 4-Cl-phenyl
7d R$^1$ = t-Bu, R$^4$ = 4-Cl-phenyl
7e R$^1$ = t-Bu; R$^4$ = CH(OCH$_3$)$_2$ Embodiments of this invention provide a concise, 6-step sequence to synthesize 4-aryl-5-pyrimidinyl imidazoles—an important scaffold useful in medicinal chemistry, such as in anticancer, antiviral, and anti-inflammatory medicinal chemistry. The methodology is well-suited to the preparation of a number of related analogs.

There are provided by the present invention methods of making amino substituted 1-(pyrimidin-4-yl)-2-phenyl-ethane-1,2-diones of Formula (I'):

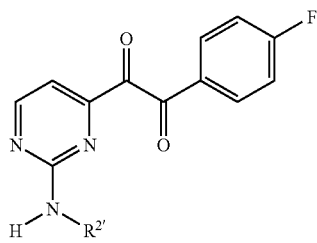

wherein
R$^{2'}$ is isopropyl or t-butyl;
comprising oxidizing an alkyne of Formula (II'):

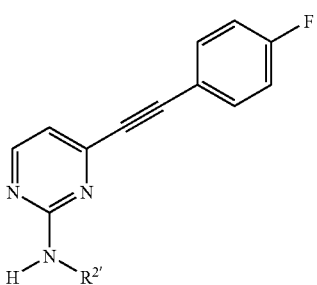

wherein R$^{2'}$ is defined as above,
with finely powdered potassium permanganate in a buffered acetone/H$_2$O solution.

The present invention further contemplates methods of making imidazoles of Formula (III'):

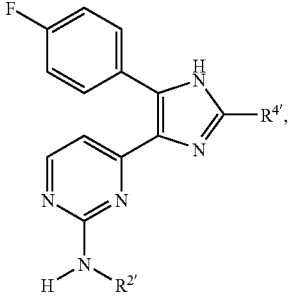

and tautomers thereof, wherein
R$^{2'}$ is defined as above; and
R$^{4'}$ is —H, 4-chlorophenyl, or —CH(OCH$_3$)$_2$;
comprising oxidizing an alkyne of Formula (II') to a 1,2-diketone of Formula (I') with finely powdered potassium permanganate in a buffered acetone/H$_2$O solution.

The present invention further contemplates methods of making compounds of Formula (I'), comprising at least one of:

a) reacting 2,4-dichloropyrimidine with (trimethylsilyl)acetylene to form 2-chloro-4-trimethylsilanylethynyl-pyrimidine;
b) reacting 2-chloro-4-trimethylsilanylethynyl-pyrimidine with R$^{2'}$NH$_2$ to form a (trimethylsilyl)alkyne of Formula (IV'):

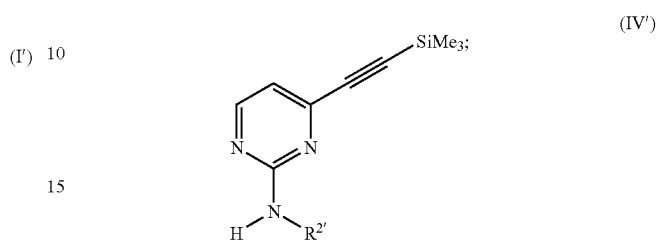

c) deprotecting a (trimethylsilyl)alkyne of Formula (IV') to form an alkyne of Formula (V'):

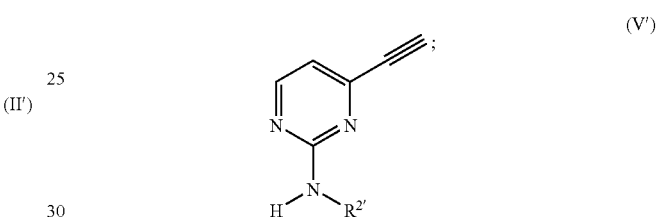

and
d) reacting an alkyne of Formula (V') with 4-iodo-fluorobenzene to form a compound of Formula (II');
wherein R$^z$ is defined as above.

The present invention further contemplates methods of making compounds of Formula (I'), comprising at least one of:

a) reacting 2,4-dichloropyrimidine with 1-ethynyl-4-fluorobenzene to form a compound of formula (VIII'):

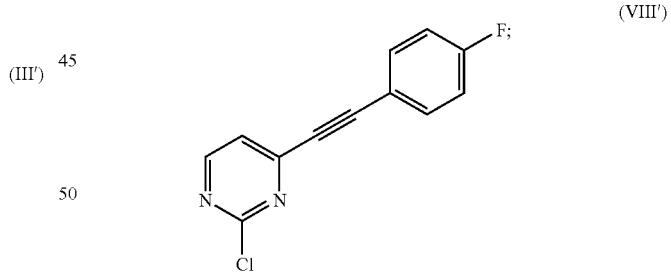

and
b) reacting a compound of formula (VIII') with R$^{2'}$NH to form a compound of Formula (II'), wherein R$^{2'}$ is defined as above.

EXAMPLES

In order to illustrate the invention, the following examples are included. These examples do not limit the invention. They are meant to suggest a method of practicing the invention. Those of ordinary skill in the art may find other methods of practicing the invention, which are obvious to them in light of the teachings provided herein. However, those methods are deemed to be within the scope of this invention.

Gas chromatograph-mass spectrometry (GC-MS) was performed on Shimazu GC-17A Gas Chromatograph and QP5000 Mass Spectrometer using electrospray ionization (ESI) in either positive or negative modes as indicated. Calculated mass corresponds to the exact mass.

NMR spectra were obtained on an INOVA-400 NMR spectrometer ($^1$H, 400 MHz; $^{13}$C, 100 MHz) or Bruker 500 NMR spectrometer ($^1$H, 500 MHz; $^{13}$C, 125 MHz) as solutions in CDCl$_3$ and were internally referenced to the solvent ($^1$H, 7.26 ppm; $^{13}$C, 77.23 ppm). The format of the $^1$H NMR data below is: chemical shift in ppm (multiplicity, coupling constant J in Hz, integration).

Infrared (IR) Spectroscopy was performed on a Nicolet 510 FT-IR with a resolution of 4 cm$^{-1}$ on dry film. IR absorptions are reported in cm$^{-1}$. Uncalibrated melting points were taken on a Thomas-Hoover melting point apparatus in open capillary tubes. Elemental analyses were performed by NuMega Resonance Labs, Inc., San Diego, Calif.

Thin-layer chromatography was performed using Merck silica gel 60 F$_{254}$ plates, eluting with 20% EtOAc/hexanes unless otherwise specified, and visualizing with UV, I$_2$, or phosphomolybdic acid stain. Normal phase flash column chromatography (FCC) was typically performed using Merck silica gel 60.

Solvents such as THF, CH$_2$Cl$_2$, and CH$_3$CN were dried over 4 A molecular sieves. The water level of dried solvents was titrated with a Fisher Coulomatic K-F titrator. Other solvents were reagent grade and used as received. Unless otherwise specified, all reactions were performed under a nitrogen atmosphere. Unless otherwise specified, reactions were performed at room temperature. Solutions were concentrated under reduced pressure on a rotary evaporator.

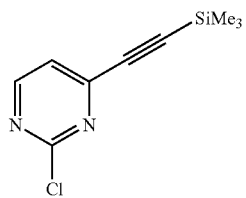

Example 1

2-Chloro-4-[trimethylsilylethynyl]pyrimidine

To a mixture of Pd(PPh$_3$)$_2$Cl$_2$ (0.9 g) and PPh$_3$ (0.7 g) in THF (200 mL) and Et$_3$N (300 mL) was added 2,4-dichloropyrimidine (40 g, 0.27 mol) under a stream of N$_2$. After bubbling N$_2$ into the solution for 15 min, CuI (0.5 g) was added, followed by (trimethylsilyl)acetylene (29 g, 0.29 mol). The mixture was heated at reflux for 4.5 h. The mixture was cooled to rt and filtered, washing with EtOAc. The filtrated was concentrated and the residue was diluted with hexanes (500 mL) and loaded directly onto a short pad of SiO$_2$. The product was eluted with 10% EtOAc/hexanes to provide a light orange solid (49.3 g), which was used without further purification. TLC: R$_f$=0.42. mp 51-54° C. IR: 3125 (w), 2961 (w), 1557 (s), 1523 (s). $^1$H NMR: 8.58 (d, J=5.0 Hz, 1H), 7.30 (d, J=5.0 Hz, 1H), 0.28 (s, 9H). $^{13}$C NMR: 162.23, 160.16, 153.41, 122.52, 104.23, 100.75, 0.01. Anal. Calcd for C$_9$H$_{11}$ClN$_2$Si: C, 51.29; H, 5.26; N, 13.29. Found: C, 51.45; H, 5.16; N, 13.33.

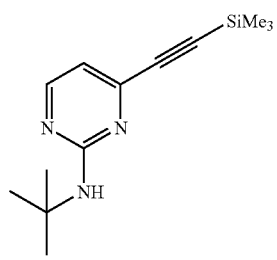

Example 2

2-tert-Butylamino-4-[trimethylsilylethynyl]pyrimidine

A mixture of 2-chloro-4-[trimethylsilylethynyl]pyrimidine (25 g, 0.12 mol) and tert-butylamine (100 mL) was heated to 80° C. for 2 d in a sealed tube. The mixture was cooled to rt and triturated with hexanes (100 mL). The resulting white precipitate was filtered and washed with hexanes. The filtrate was concentrated to give the crude product as a brown oil, which was used in the following reaction without further purification. TLC: R$_f$=0.40. mp 71-73° C. IR: 3293 (br, w), 2962 (w), 1569 (s). $^1$H NMR: 8.22 (d, J=5.0 Hz, 1H), 6.57 (d, J=5.0 Hz, 1H), 5.19 (s, 1H), 1.42 (s, 9H), 0.26 (s, 9H). $^{13}$C NMR: 162.38, 158.15, 150.95, 112.94, 102.77, 97.62, 51.41, 29.25, −0.11. Anal. Calcd for C$_{13}$H$_{21}$N$_3$Si: C, 63.11; H, 8.56; N, 16.98. Found: C, 63.20; H, 8.52; N, 16.70.

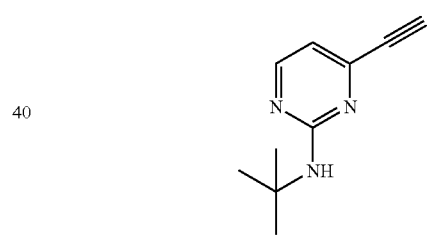

Example 3 tert-Butylamino-4-ethynylpyrimidine

A solution of 2-tert-butylamino-4-[trimethylsilylethynyl]pyrimidine (from Example 2) in CH$_3$OH (150 mL) was treated with a solution of KOH (30 mg) in CH$_3$OH (5 mL). After 30 min, additional KOH (30 mg) in CH$_3$OH (5 mL) was added. After a further 30 min, the mixture was concentrated and the residue was diluted with hexanes and loaded directly onto a short pad of SiO$_2$. The product was eluted with 10% EtOAc in hexanes to provide the crude product as a light brown oil (18.6 g, 90% for 2 steps), which was used without further purification. TLC: R$_f$=0.29. IR: 3294 (m), 2965 (m), 2114 (w), 1571 (s). $^1$H NMR: 8.23 (d, J=5.0 Hz, 1H), 6.60 (d, J=5.0 Hz, 1H), 5.20 (s, 1H), 3.15 (s, 1H), 1.43 (s, 9H). $^{13}$C NMR: 161.97, 157.99, 149.87, 112.63, 81.71, 78.72, 51.06, 28.80.

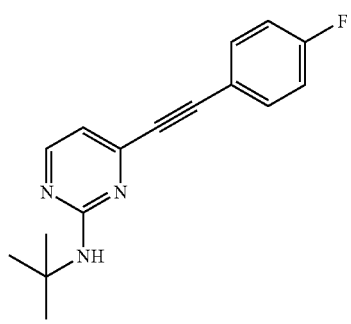

Example 4

2-tert-Butylamino-4-[4-fluoro-phenylethynyl]pyrimidine

To a mixture of Pd(PPh$_3$)Cl$_2$ (0.4 g) in Et$_3$N (150 mL) and THF (150 mL) under a stream of N$_2$, was added tert-butylamino-4-ethynylpyrimidine (18.6 g, 0.11 mol). After bubbling N$_2$ into the solution for 15 min, 4-iodo-fluorobenzene (23.6 g, 0.11 mol) and CuI (0.22 g) were added sequentially. The mixture was stirred at rt for 2.5 h. The precipitate was filtered and washed with EtOAc. The filtrate was concentrated and the residue was diluted with EtOAc and loaded directly onto a short pad of silica gel. The product was eluted with 10% EtOAc in hexanes to afford the crude product, which was recrystallized from EtOAc/hexanes to give the title compound as a light yellow solid (25 g, 84%). TLC: R$_f$=0.30. mp 97-99° C. IR: 3287 (w), 2964 (w), 2222 (w), 1566 (s). $^1$H NMR: 8.26 (d, J=4.2 Hz, 1H), 7.60-7.55 (m, 2H), 7.10-7.00 (m, 2H), 6.65 (d, J=4.9 Hz, 1H), 5.22 (s, 1H), 1.45 (s, 9H). $^{13}$C NMR: 164.19, (162.19, 162.03), 157.77, 150.83, (134.35, 134.29), (117.84, 117.81), (115.94, 115.76), 112.37, 89.91, 87.24, 51.07, 28.86. Anal. Calcd for C$_{16}$H$_{16}$FN$_3$: C, 71.36; H, 5.99; N, 15.60. Found: C, 71.25; H, 5.95; N, 15.66.

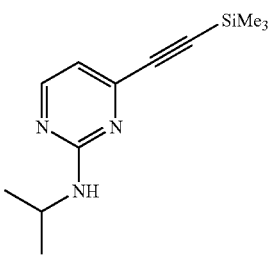

Example 5

1-(2-tert-Butylamino-pyrimidin-4-yl)-2-(4-fluoro-phenyl)-ethane-1,2-dione

To a solution of 2-tert-butylamino-4-[4-fluoro-phenylethynyl]pyrimidine (5.0 g, 19 mmol) in acetone (225 mL) was added a solution of NaHCO$_3$ (0.40 g) and MgSO$_4$ (4.0 g) in H$_2$O (120 mL). Under vigorous stirring, KMnO$_4$ (Cairox M from Carux Co.; 11.1 g, 70 mmol) was added at rt in one portion. After 4 min, the reaction was quenched by the addition of NaHSO$_3$ (15 g) in H$_2$O (30 mL). After stirring for 10 min, the mixture was acidified with 50% H$_2$SO$_4$ to pH<2, and extracted with 1:1 Et$_2$O/hexanes (300 mL) and EtOAc (50 mL). The combined organic layers were washed with aq. K$_2$CO$_3$ (1 mol/L, saturated with NaCl; 100 mL) and brine (100 mL), dried (Na$_2$SO$_4$), and concentrated to provide the diketone as a light yellow solid (4.0 g, 71%). TLC: R$_f$=0.15. mp 123-124° C. IR: 3297 (br w), 2968 (w), 1711 (m) 1680 (m), 1596 (s), 1583 (s). $^1$H NMR (95% purity): 8.54 (d, J=3.4 Hz, 1H), 8.0-7.90 (m, 2H), 7.22-7.12 (m, 3H), 5.29 (s, 1H), 1.18 (s, 9H). $^{13}$C NMR: 195.22, 167.89, 165.33, (161.80, 160.37), 157.56, (132.12, 132.02), (129.72, 129.70), (116.45, 116.23), 106.42, 51.11, 28.25. Anal. Calcd for C$_{16}$H$_{16}$FN$_3$O$_2$: C, 63.78; H, 5.35; N, 13.95. Found: C, 63.85; H, 5.22; N, 13.94.

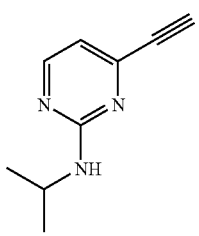

Example 6

2-iso-Propylamino-4-[trimethylsilylethynyl]pyrimidine

The title compound was prepared according to the methods described in Example 2, substituting isopropylamine for tert-butylamine. TLC: R$_f$=0.31. mp 93-94° C. IR: 3273 (br w), 2967 (m), 1570 (s). $^1$H NMR: 8.23 (d, J=5.0 Hz, 1H), 6.59 (d, J=5.0 Hz, 1H), 5.02 (d, J=5.5 Hz, 1H), 4.14 (sept, J=6.4 Hz, 1H), 1.21 (d, J=6.4 Hz, 6H), 0.25 (s, 9H). $^{13}$C NMR: 162.06, 158.68, 151.33, 113.21, 102.70, 98.14, 43.20, 23.28, 0.10.

Example 7

2-iso-Propylamino-4-ethynylpyrimidine

The title compound was prepared according to the methods described in Example 3, substituting 2-iso-propylamino-4-[trimethylsilylethynyl]pyrimidine for tert-butylamino-4-ethynylpyrimidine (92% for 2 steps). TLC: R$_f$=0.24. mp 84-85° C. IR: 3256 (br, m), 2974 (w), 2113 (w), 1568 (s). $^1$H NMR: 8.25 (d, J=5.0 Hz, 1H), 6.62 (d, J=5.0 Hz, 1H), 5.05 (s, 1H), 4.14 (sept, J=6.5 Hz, 1H), 3.19 (s, 1H), 1.22 (d, J=6.5 Hz, 6H). $^{13}$C NMR: 162.05, 158.84, 150.66, 113.22, 81.98, 79.54, 43.19, 23.20. Anal. Calcd for $C_9H_{11}N_3$: C, 67.04; H, 6.88; N, 26.07. Found: C, 67.38; H, 6.88; N, 26.32.

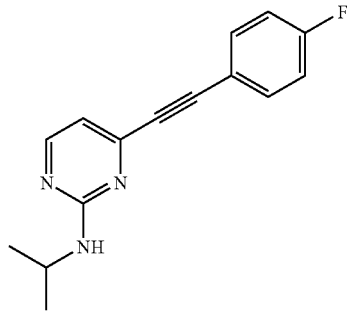

Example 8

2-iso-Propylamino-4-[4-fluoro-phenylethynyl]pyrimidine

The title compound was prepared according to the methods described for Example 4 (89% yield). TLC: $R_f$=0.19. mp 128-129° C. IR: 3260 (br w), 2970 (s), 2216 (w), 1564 (s). $^1$H NMR: 8.28 (d, J=4.6 Hz, 1H), 7.60-7.50 (m, 2H), 7.10-7.00 (m, 2H), 6.66 (d, J=4.9 Hz, 1H), 5.05 (d, J=7.4 Hz, 1H), 4.17 (sept, J=6.5 Hz, 1H), 1.24 (d, J=6.5 Hz, 6H). $^{13}$C NMR: 164.23, (162.23, 161.71), 158.27, 151.24, (134.39, 134.32), (117.76, 117.74), (115.96, 115.78), 112.62, 90.37, 87.18, 42.84, 22.89. Anal. Calcd for $C_{15}H_{14}FN_3$: C, 70.57; H, 5.53; N, 16.46. Found: C, 70.60; H, 5.42; N, 16.45.

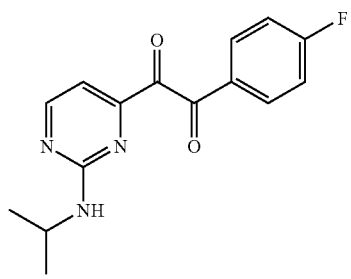

Example 9

1-(2-iso-Propylamino-pyrimidin-4-yl)-2-(4-fluorophenyl)-ethane-1,2-dione

The title compound was prepared according to the methods described in Example 5 (90% yield). TLC: $R_f$=0.14. mp 75-77° C. IR: 3275 (br, w), 2971 (w), 1710 (m), 1682 (m). $^1$H NMR (90% purity): 8.57 (s, 1H), 8.00-7.90 (m, 2H), 7.23-7.15 (m, 3H), 5.08 (s, 1H), 3.73 (br s, 1H), 1.09 (s, 6H). Anal. Calcd for $C_{15}H_{14}FN_3O_2$: C, 62.71; H, 4.91; N, 14.63. Found: C, 62.90; H, 4.84; N, 14.76.

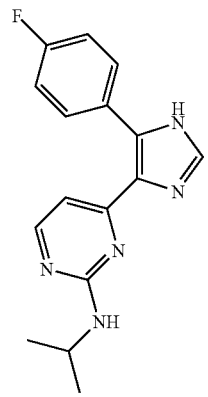

Example 10 tert-Butyl-{4-[5-(4-fluoro-phenyl)-1H-imidazol-4-yl]-pyrimidin-2-yl}-amine

A mixture of 1-(2-iso-propylamino-pyrimidin-4-yl)-2-(4-fluoro-phenyl)-ethane-1,2-dione (12.5 g, 43.5 mmol), hexamethylenetetramine (12.2 g, 87.1 mmol), $NH_4OAc$ (17 g, 220 mmol), and $Na_2SO_4$ (12 g) in AcOH (150 mL) was heated at 65° C. After 4 h, the mixture was cooled to rt. The mixture was filtered, washing with AcOH. The filtrate was concentrated, and the residue was dissolved in $CH_2Cl_2$. The organic solution was washed with 1 N NaOH, dried ($Na_2SO_4$), and concentrated. The crude product was purified by column chromatography (MeOH/hexanes) to afford the title compound as a light yellow solid (6.8 g, 52%). TLC (10% MeOH/$CH_2Cl_2$): $R_f$=0.21. $^1$H NMR: 8.13 (br s, 1H), 7.84 (br s, 1H), 7.61 (br s, 2H), 7.14 (t, J=7.8 Hz, 2H), 6.87 (br s, 1H), 5.31 (br s, 1H), 4.14 (br s, 1H), 1.26 (d, J=9.8 Hz, 6H). HRMS (ESI): [M+H]$^+$ calcd. for $C_{16}H_{17}FN_5$, 298.1463; found, 298.1461.

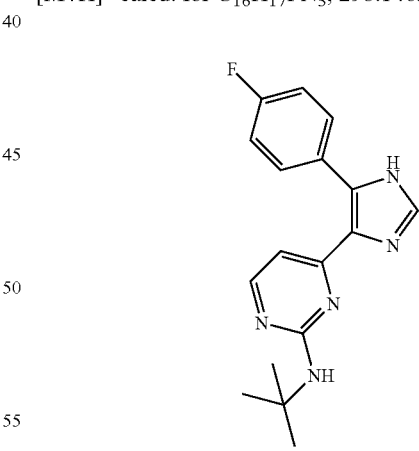

Example 11 tert-Butyl-{4-[5-(4-fluoro-phenyl)-1H-imidazol-4-yl]-pyrimidin-2-yl}-amine

The title compound was prepared from 1-(2-tert-butylamino-pyrimidin-4-yl)-2-(4-fluoro-phenyl)-ethane-1,2-dione according to the methods described in Example 10 (56%). TLC (10% MeOH/$CH_2Cl_2$): $R_f$=0.22. $^1$H NMR: 8.04

(d, J=5.3 Hz, 1H), 7.75 (br s, 1H), 7.56 (dd, J=8.5, 5.5 Hz, 2H), 7.12 (t, J=8.6 Hz, 2H), 6.63 (d, J=5.3 Hz, 1H), 5.76 (br s, 1H), 1.45 (s, 9H). $^{13}$C NMR: 163.75, (161.78, 161.47), 157.33, 156.21, 140.42, 135.61, (130.97, 130.90), (130.07, 130.05), 126.13, (115.63, 115.46), 105.31, 50.86, 28.98. HRMS (ESI): [M+H]$^+$ calcd. for $C_{17}H_{19}FN_5$, 312.1619; found, 312.1631.

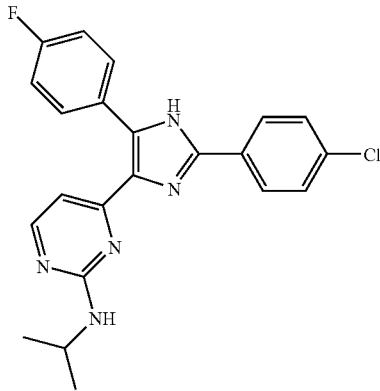

Example 12

{4-[2-(4-Chloro-phenyl)-5-(4-fluoro-phenyl)-1H-imidazol-4-yl]-pyrimidin-2-yl}-isopropyl-amine The title compound was prepared from 1-(2-iso-propylamino-pyrimidin-4-yl)-2-(4-fluoro-phenyl)-ethane-1,2-dione, 4-chlorobenzaldehyde, and NH$_4$OAc according to the methods described in Example 10 (62%). The reaction time was 48 h. TLC (50% EtOAc/hexanes): R$_f$=0.44. $^1$H NMR: 10.52 (br s, 1H), 8.11 (d, J=5.2 Hz, 1H), 7.87 (d, J=8.5 Hz, 2H), 7.61 (dd, J=7.6, 5.8 Hz, 2H), 7.42 (d, J=8.5 Hz, 2H), 7.13 (d, J=8.5 Hz, 2H), 6.61 (br s, 1H), 5.22 (br s, 1H), 4.17 (br s, 1H), 1.25 (br s, 6H). $^{13}$C NMR: 163.86, 161.88, 161.41, 158.06, 145.59, 135.41, (131.08, 131.02), 129.17, 126.84, (115.63, 115.46), 105.59, 42.83, 22.89 (weak signals for some carbon members). HRMS (ESI): [M+H]$^+$ calcd. for $C_{22}H_{20}ClFN_5$, 408.1386; found, 408.1404.

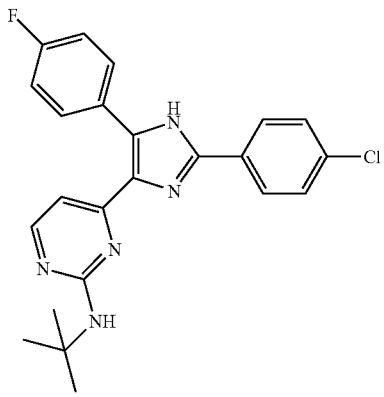

Example 13 tert-Butyl-{4-[2-(4-chloro-phenyl)-5-(4-fluoro-phenyl)-1H-imidazol-4-yl]-pyrimidin-2-yl}-amine The title compound was prepared from 1-(2-tert-butylamino-pyrimidin-4-yl)-2-(4-fluoro-phenyl)ethane-1,2-dione, 4-chlorobenzaldehyde, and NH$_4$OAc according to the methods described in Example 12 (68%). TLC (50% EtOAc/hexanes): R$_f$=0.60. $^1$H NMR: 10.52 (br s, 1H), 8.10 (d, J=4.7 Hz, 1H), 7.82 (d, J=8.5 Hz, 2H), 7.65 (br s, 2H), 7.40 (d, J=8.3 Hz, 2H), 7.12 (br s, 2H), 6.58 (br s, 1H), 5.29 (br s, 1H), 1.49 (s, 9H). $^{13}$C NMR: 163.79, (161.82, 161.77), 157.86, 145.48, 135.32, (130.99, 130.93), 129.15, 127.68, 126.71, (115.63, 115.45), 105.32, 50.86, 29.02 (weak signals for some carbon members). HRMS (ESI): [M+H]$^+$ calcd. for $C_{23}H_{22}ClFN_5$, 422.1542; found, 422.1563.

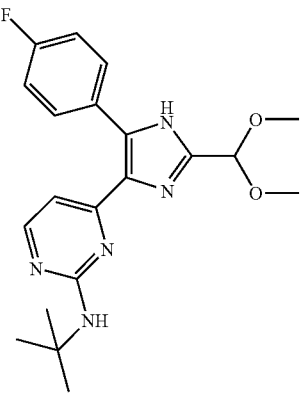

Example 14 tert-Butyl-{4-[2-dimethoxymethyl-5-(4-fluoro-phenyl)-1H-imidazol-4-yl]-pyrimidin-2-yl}-amine The title compound was prepared from 1-(2-tert-butylamino-pyrimidin-4-yl)-2-(4-fluoro-phenyl)-ethane-1,2-dione, glyoxal 1,1-dimethylacetal, and NH$_4$OAc, using tert-butyl methyl ether as the solvent, according to the methods described in Example 10 (20%). The reaction time was 48 h at rt. TLC (50% EtOAc/hexanes): R$_f$=0.19. $^1$H NMR (CDCl$_3$): 10.29 (br s, 1H), 8.07 (d, J=5.2 Hz, 1H), 7.60 (dd, J=8.0, 5.6 Hz, 2H), 7.11 (t, J=8.6 Hz, 2H), 6.57 (d, J=5.2 Hz, 1H), 5.55 (s, 1H), 5.23 (br s, 1H), 3.46 (s, 6H), 1.49 (s, 9H). $^{13}$C NMR (CDCl$_3$): 163.73, (161.87, 161.76), 157.88, 155.38, 145.20, 142.04, (131.03, 130.97), 130.69, 124.84, (115.50, 115.33), 105.33, 98.08, 53.60, 50.87, 29.04. MS (ESI): [M+H]$^+$ calcd. for $C_{20}H_{24}FN_5O_2$, 385.19; found, 386.1.

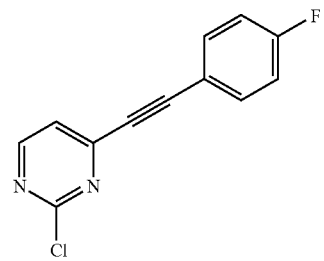

Example 15

2-Chloro-4-(4-fluoro-phenylethynyl)-pyrimidine

The title compound was prepared from 2,4-dichloropyrimidine and 1-ethynyl-4-fluorobenzene using methods analogous to those described in Example 2 (65%). TLC (25% EtOAc/hexanes): $R_f$=0.21. mp 125-126° C. IR: 3049 (w), 2210 (w), 1559 (s). $^1$H NMR (CDCl$_3$): 8.61 (d, J=5.0 Hz, 1H), 7.70-7.60 (m, 2H), 7.38 (d, J=5.0 Hz, 1H), 7.13-7.06 (m, 2H). $^{13}$C NMR (CDCl$_3$): 163.99 (d, $J_{C-F}$=252 Hz), 161.86, 159.66, 153.39, 134.96 (d, $J_{C-F}$=8.6 Hz), 121.77, 116.96 (d, JC-F=3.4 Hz), 116.40 (d, $J_{C-F}$=22 Hz), 95.27, 85.89. Anal. Calcd for C$_{12}$H$_6$ClFN$_2$: C, 61.95; H, 2.60; N, 12.04. Found: C, 62.15; H, 2.83; N, 12.00.

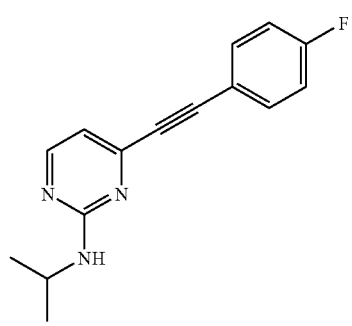

Example 16

Alternative preparation for 2-iso-Propylamino-4-[4-fluoro-phenylethynyl]pyrimidine A solution of 2-chloro-4-(4-fluoro-phenylethynyl)-pyrimidine (1 equiv.) in iso-propylamine (0.2 M) is heated at 35° C. for 24 h. The mixture is cooled to rt, diluted with water, and extracted with EtOAc. The organic layer is concentrated and the residue purified by column chromatography to provide the title compound.

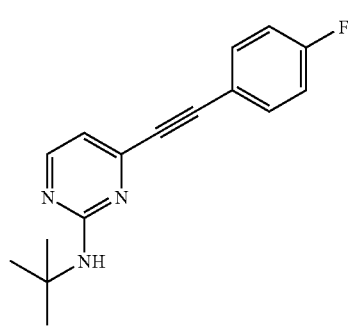

Example 17

Alternative preparation for 2-tert-Butylamino-4-[4-fluoro-phenylethynyl]pyrimidine A solution of 2-chloro-4-(4-fluoro-phenylethynyl)-pyrimidine (1 equiv.) in tert-butylamine (0.2 M) is heated at 80° C. in a sealed tube for 24 h. The mixture is cooled to rt, diluted with water, and extracted with EtOAc. The organic layer is concentrated and the residue purified by column chromatography to provide the title compound.

The compounds in Examples 18-21 may be prepared using the methods described in the preceding examples.

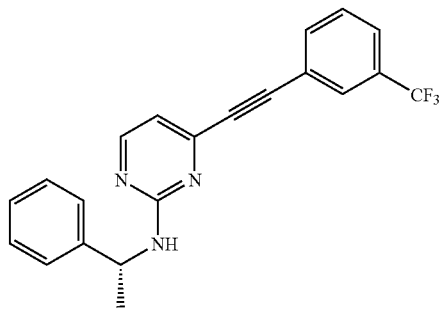

Example 18

(R)-(1-Phenyl-ethyl)-[4-(3-trifluoromethyl-phenyl-ethynyl)-pyrimidin-2-yl]-amine

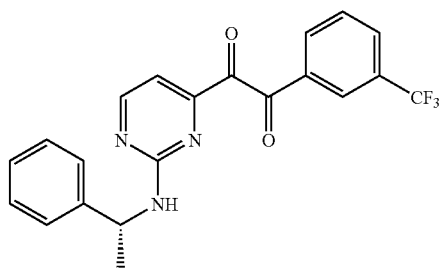

Example 19

(R)-1-[2-(1-Phenyl-ethylamino)-pyrimidin-4-yl]-2-(3-trifluoromethyl-phenyl)-ethane-1,2-dione

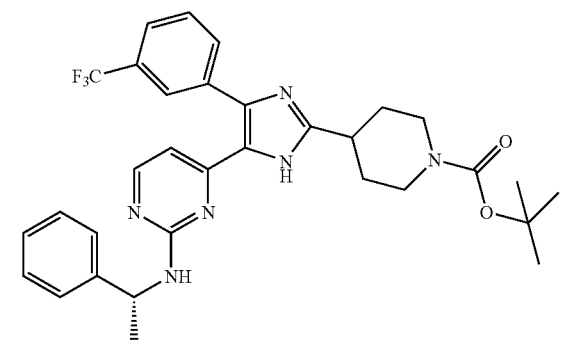

Example 20

(R)-4-[5-[2-(1-Phenyl-ethylamino)-pyrimidin-4-yl]-4-(3-trifluoromethyl-phenyl)-1H-imidazol-2-yl]-piperidine-1-carboxylic acid tert-butyl ester Deprotection and alkylation methods known in the art may be used to convert Example 20 into compound 2.

What is claimed is:

1. A method of making pyrimidinyl-substituted imidazole compounds, comprising: reacting 2,4-dichloropyrimidine with a nucleophilic-attack-protected acetylene to form 2-chloro-4-protected-ethynyl-pyrimidine.

2. A method as recited in claim 1, wherein said nucleophilic-attack-protected acetylene is [(tri-$C_{1-4}$-alkyl)silyl]acetylene and said 2-chloro-4-protected-ethynyl-pyrimidine is 2-chloro-4-(tri-$C_{1-4}$-alkylsilanylethynyl)pyrimidine.

3. A method as recited in claim 2, wherein said [(tri-$C_{1-4}$alkyl)silyl]acetylene is (trimethylsilyl)acetylene and said 2-chloro-4-(tri-$C_{1-4}$alkylsilanylethynyl)pyrimidine is 2-chloro-4-trimethylsilanylethynyl-pyrimidine.

4. A method of making a compound of Formula (III') or a tautomer thereof, comprising:
reacting 2,4-dichloropyrimidine with a nucleophilic-attack-protected acetylene to form 2-chloro-4-protected-ethynyl-pyrimidine; wherein said nucleophilic-attack-protected acetylene is (trimethylsilyl)acetylene, and said 2-chloro-4-protected-ethynyl-pyrimidine is 2-chloro-4-trimethylsilanylethynyl-pyrimidine;

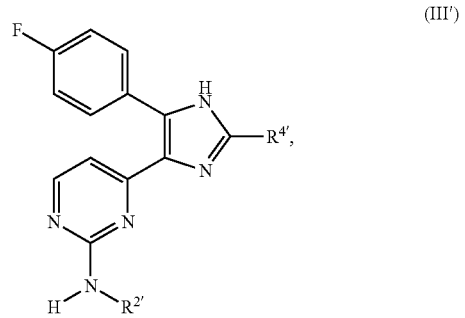

(III')

wherein $R^{2'}$ is isopropyl or t-butyl, and $R^{4'}$ is H, 4-chlorophenyl, or —CH(OCH$_3$)$_2$.

5. A method as recited in claim 4, further comprising:
reacting said 2-chloro-4-trimethylsilanylethynyl-pyrimidine with $R^{2'}NH_2$ to form a (trimethylsilyl)alkyne of Formula (IV'):

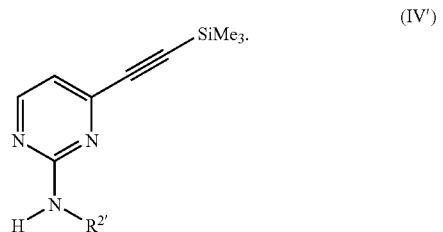

(IV')

6. A method as recited in claim 5, further comprising:
deprotecting the (trimethylsilyl)alkyne of Formula (IV') to form an alkyne of Formula (V'):

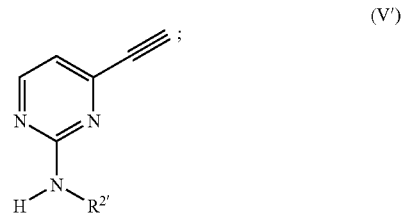

(V')

and
reacting the alkyne of Formula (V') with 4-iodo-fluorobenzene to form an alkyne of Formula (II'):

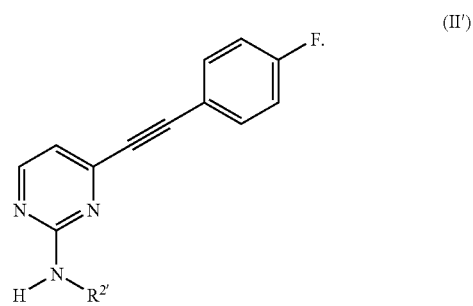

(II')

7. A method as recited in claim 6, further comprising:
oxidizing the alkyne of Formula (II') with finely powdered potassium permanganate in a buffered solution to form a 1,2-diketone of Formula (I'):

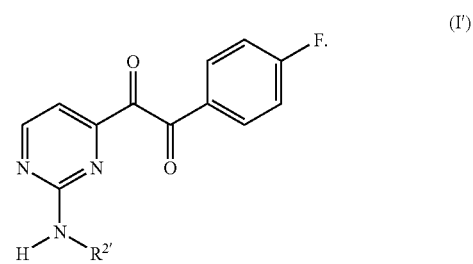

(I')

8. A method as recited in claim 7, further comprising:
reacting said 1,2-diketone of Formula (I') in the presence of an ammonia equivalent with at least one of $R^4CHO$ and a formaldehyde equivalent to generate a compound of Formula (III').

9. A method as recited in claim 8, wherein said ammonia equivalent is selected from the group consisting of ammonia, ammonium acetate, and mixtures thereof.

10. A method as recited in claim 7, wherein said formaldehyde equivalent is selected from the group consisting of hexamethylenetetramine, formaldehyde, and mixtures thereof.

11. A method as recited in claim 7, wherein said buffered solution is buffered at a pH of about 7.5.

12. A method as in claim 3, wherein a compound of Formula (III) is formed:

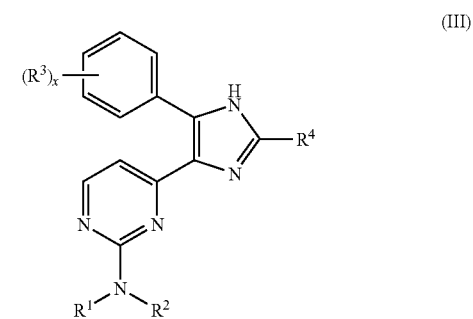

(III)

wherein:

R$^1$ and R$^2$ are each independently selected from the group consisting of —H, —C$_{1-6}$alkyl, —C$_{3-8}$cycloalkyl, benzyl, and 1-methylbenzyl;

x is 0, 1, 2, or 3;

each R$^3$ is independently selected from the group consisting of —OH, —Cl, —F, —C$_{1-6}$alkyl, —C$_{3-8}$cycloalkyl, —OC$_{1-6}$alkyl, —CF$_3$, —OCF$_3$, phenyl, —CN, —NO$_2$, —N(R$^a$)R$^b$, —C(O)N(R$^a$)R$^b$, —N(R$^c$)C(O)R$^d$, —N(R$^c$)SO$_2$C$_{1-6}$alkyl, —C(O)C$_{1-6}$alkyl, —S(O)$_{0-2}$C$_{1-6}$alkyl, —SO$_2$N(R$^a$)R$^b$, —CO$_2$H, and —CO$_2$C$_{1-6}$alkyl, where R$^a$ and R$^b$ are each independently —H or —C$_{1-6}$alkyl, and where R$^c$ and R$^d$ are each independently —H or —C$_{1-6}$alkyl; and R$^4$ is —H, —C$_{1-8}$alkyl, —C$_{3-8}$cycloalkyl, aryl, heteroaryl, or —CH(OC$_{1-6}$alkyl)$_2$;

or tautomers, enantiomers, diastereomers, or pharmaceutically acceptable salts or esters thereof.

13. A method as recited in claim 12, further comprising:

reacting 2-chloro-4-trimethylsilanylethynyl-pyrimidine with R$^1$R$^2$NH to form a (trimethylsilyl)alkyne of Formula (IV):

(IV)

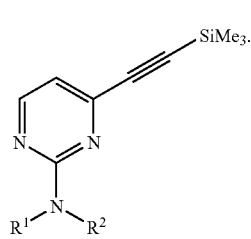

14. A method as recited in claim 13, further comprising:

deprotecting the (trimethylsilyl)alkyne of Formula (IV) to form an alkyne of Formula (V):

(V)

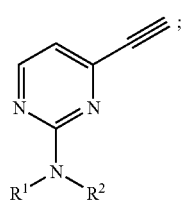

and reacting the alkyne of Formula (V) with a compound of Formula (VI):

(VI)

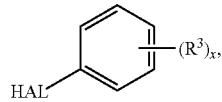

to form an alkyne of Formula (II):

(II)

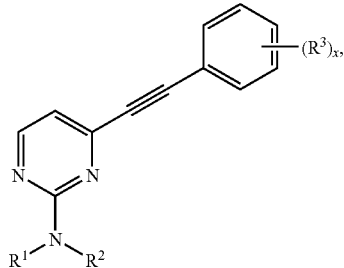

wherein HAL is I or Br.

15. A method as recited in claim 14, further comprising:

oxidizing the alkyne of Formula (II) with finely powdered potassium permanganate to form a 1,2-diketone of Formula (I):

(I)

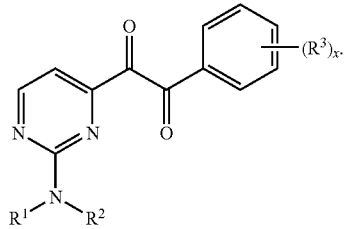

16. A method as recited in claim 15, further comprising:

reacting said 1,2-diketone of Formula (I) in the presence of an ammonia equivalent with at least one of R$^4$—CHO and a formaldehyde equivalent.

17. A method as recited in claim 16, wherein said ammonia equivalent is selected from the group consisting of ammonia, ammonium acetate, and mixtures thereof.

18. A method as recited in claim 16, wherein said formaldehyde equivalent is selected from the group consisting of hexamethylenetetramine, formaldehyde, and mixtures thereof.

19. A method as recited in claim 16, wherein said oxidizing the alkyne of Formula (II) is performed in a buffered solution, and said buffered solution is buffered at a pH in the range from about 7 to about 8.

* * * * *